US012754161B2

(12) United States Patent
Watanabe et al.

(10) Patent No.: US 12,754,161 B2

(45) Date of Patent: Oct. 6, 2026

(54) SENSOR ELEMENT

(71) Applicant: NGK INSULATORS, LTD., Nagoya (JP)

(72) Inventors: Yusuke Watanabe, Nagoya (JP); Takayuki Sekiya, Nisshin (JP); Shotaro Niizuma, Kasugai (JP); Hayami Aota, Nagoya (JP); Toshihiro Hirakawa, Kasugai (JP)

(73) Assignee: NGK INSULATORS, LTD., Nagoya (JP)

( * ) Notice: Subject to any disclaimer, the term of this patent is extended or adjusted under 35 U.S.C. 154(b) by 17 days.

(21) Appl. No.: 17/702,018

(22) Filed: Mar. 23, 2022

(65) Prior Publication Data

US 2022/0308011 A1 Sep. 29, 2022

(30) Foreign Application Priority Data

Mar. 29, 2021 (JP) ................................ 2021-056171
Feb. 10, 2022 (JP) ................................ 2022-019967

(51) Int. Cl.
*G01N 27/41* (2006.01)
*G01N 33/00* (2006.01)

(52) U.S. Cl.
CPC ......... *G01N 27/41* (2013.01); *G01N 33/0037* (2013.01)

(58) Field of Classification Search
CPC ................. G01N 27/41; G01N 27/417; G01N 27/4071; G01N 27/4072; G01N 27/4162; G01N 33/0037
See application file for complete search history.

(56) References Cited

U.S. PATENT DOCUMENTS 5,763,763 A 6/1998 Kato et al.
5,893,968 A * 4/1999 Kato .................... G01N 27/419 73/23.31

(Continued)

FOREIGN PATENT DOCUMENTS

JP 3050781 B2 6/2000
JP 2004-93200 A 3/2004

(Continued)

OTHER PUBLICATIONS

Unexamined U.S. Appl. No. 17/702,005, filed Mar. 23, 2022.2022.

(Continued)

*Primary Examiner* — Shizhi Qian
(74) *Attorney, Agent, or Firm* — MATTINGLY & MALUR, PC

(57) ABSTRACT

A sensor element includes a base part including a plurality of oxygen-ion-conductive solid electrolyte layers stacked; a measurement-object gas flow part for introduction and flow of a measurement-object gas through a gas inlet; an inner oxygen pump electrode disposed on an inner surface of the measurement-object gas flow part; and a measurement electrode disposed on the inner surface of the measurement-object gas flow part. The inner oxygen pump electrode includes: a region (A) including an electrode end close to the gas inlet, and a region (B) including an electrode end far from the gas inlet. A content rate of an activity reducing metal in a metal material in the region (A) is higher than that in the region (B). A ratio of the length of the region (A) of the inner oxygen pump electrode to the length of the inner oxygen pump electrode is 15% to 90%.

9 Claims, 11 Drawing Sheets

(56) References Cited

U.S. PATENT DOCUMENTS

| | | | | |
|---|---|---|---|---|
| 2004/0069629 | A1 | 4/2004 | Tanaka et al. | |
| 2009/0242402 | A1* | 10/2009 | Horisaka ............ | G01N 33/0037 204/412 |
| 2010/0243447 | A1* | 9/2010 | Fujisaki ............. | G01N 27/4075 204/292 |
| 2011/0147214 | A1 | 6/2011 | Fujita et al. | |
| 2019/0137441 | A1* | 5/2019 | Nakagaki ........... | G01N 27/4071 |
| 2020/0041442 | A1* | 2/2020 | Watanabe .......... | G01N 27/4072 |
| 2020/0064302 | A1* | 2/2020 | Sekiya ............... | G01N 27/4075 |
| 2020/0200700 | A1 | 6/2020 | Okamoto et al. | |

FOREIGN PATENT DOCUMENTS

| | | | |
|---|---|---|---|
| JP | 2014-190940 | A | 10/2014 |
| JP | 2014-209128 | A | 11/2014 |
| JP | 2020-101493 | A | 7/2020 |

OTHER PUBLICATIONS

Unexamined U.S. Appl. No. 17/702,014, filed Mar. 23, 2022.

Japanese Office Action received in corresponding Japanese Application No. 2022-019967 dated Jun. 17, 2025.

* cited by examiner

SENSOR ELEMENT

CROSS-REFERENCE TO RELATED APPLICATION

The present application claims priority from Japanese applications JP2021-056171, filed on Mar. 29, 2021 and JP2022-019967, filed Feb. 10, 2022, the contents of which are hereby incorporated by reference into this application.

BACKGROUND OF THE INVENTION

Technical Field of the Invention

The present invention relates to a sensor element using an oxygen ion conductive solid electrolyte.

Background Art

A gas sensor is used for detection or measurement of concentration of an objective gas component (oxygen $O_2$, nitrogen oxide NOx, ammonia $NH_3$, hydrocarbon HC, carbon dioxide $CO_2$, etc.) in a measurement-object gas, such as exhaust gas of automobile. For example, conventionally, the concentration of the objective gas component in exhaust gas of an automobile is measured, and an exhaust gas cleaning system mounted on the automobile is optimally controlled based on the measurement.

As such a gas sensor, a gas sensor equipped with a sensor element using an oxygen ion conductive solid electrolyte such as zirconia ($ZrO_2$) is known. The gas sensor detects an electromotive force or a current value corresponding to the concentration of an objective gas component in a measurement-object gas by using the oxygen ion conductivity of the solid electrolyte, thereby detecting the gas component and measuring the concentration.

For example, JP3050781B2 discloses a gas sensor that controls the oxygen partial pressure to such a low level that does not substantially affect measurement of the amount of a measurement-object gas component by means of a first electrochemical pumping cell and a second electrochemical pumping cell, and detects a current value corresponding to the oxygen generated by reduction or decomposition of the measurement-object gas component. In other words, oxygen is preliminarily removed by the first electrochemical pumping cell and the second electrochemical pumping cell, and the oxygen derived from the objective gas component (for example, nitrogen oxide NOx) is detected.

JP3050781B2 also indicates that the concentration of nitrogen oxide (NOx) and the detected current value have a linear relationship (FIG. 5).

JP2014-209128A and JP2014-190940A disclose a NOx sensor. In the disclosure, the NOx sensor has a main pump cell and an auxiliary pump cell for adjusting oxygen concentration, and as an inner pump electrode of the main pump cell, for example, a cermet electrode of Pt containing 1% Au and zirconia is used.

CITATION LIST

Patent Documents

Patent Document 1: JP3050781B2
Patent Document 2: JP2014-209128A
Patent Document 3: JP2014-190940A

SUMMARY OF THE INVENTION

Problems to be Solved by the Invention

In a conventional gas sensor, for example, as disclosed in JP2014-209128A, a measurement-object gas is introduced into an internal space of the sensor element through the gas inlet in one end part in the longitudinal direction of the sensor element. Then, an oxygen partial pressure in the measurement-object gas is controlled by the main pump cell and the auxiliary pump cell to such a low level that does not substantially affect measurement of a target gas to be measured (for example, NOx) in the measurement electrode. In that state, oxygen generated by decomposition of NOx is detected as a current value in the measurement pump cell. That is, oxygen and NOx in the measurement-object gas are separated from each other, and then oxygen generated from NOx is detected.

In such a gas sensor, it is required that NOx is not decomposed in the main pump cell and the auxiliary pump cell. Therefore, each pump electrode that is disposed on the inner surface of the internal space of the sensor element, and constitutes each one electrode of the main pump cell and the auxiliary pump cell is made of a material that does not decompose NOx. As a material that does not decompose NOx, a metal material in which Au is added to Pt is known (JP2014-209128A, JP2014-190940A).

It was however found that NOx may decompose in a pump electrode constituting the main pump cell when oxygen of high concentration is present in the measurement-object gas, and this may result in decrease in NOx detection accuracy.

In light of this, it is an object of the present invention to provide a sensor element capable of maintaining high NOx detection accuracy regardless of the oxygen concentration in the measurement-object gas.

Means for Solving the Problems

The present inventors diligently studied about the mechanism of decrease in NOx detection accuracy under high oxygen concentration, and considered as follows. When oxygen of high concentration is present in the measurement-object gas introduced through the gas inlet, it is necessary to discharge most of the oxygen of high concentration from the internal space of the sensor element by the main pump cell. In particular, since oxygen of high concentration is discharged by pumping at a position close to the gas inlet in the pump electrode, the applied voltage locally increases. When a high voltage is locally applied, NOx in the measurement-object gas may be decomposed in the part of the pump electrode where the high voltage is applied. This leads to reduction in the amount of NOx that reaches the measurement electrode for detecting NOx. As a result, the NOx detection accuracy decreases.

As described above, in the gas sensor that detects NOx in the measurement-object gas, the oxygen pump cell (configured, for example, by the main pump cell and the auxiliary pump cell) adjusts the oxygen partial pressure in the measurement-object gas introduced into the internal space of the sensor element through the gas inlet. Then, the measurement pump cell detects NOx in the measurement-object gas whose oxygen partial pressure has been adjusted.

In such a gas sensor, it was found that the inner oxygen pump electrode that constitutes the oxygen pump cell and comes into contact with the measurement-object gas introduced into the internal space of the sensor element needs to further suppress decomposition of NOx especially at a position close to the gas inlet of the sensor element.

The present inventors found that by configuring a specific region close to the gas inlet of the sensor element in the inner oxygen pump electrode to contain more activity reducing metal that reduces the catalytic activity of decomposing NOx than the region far from the gas inlet, it is possible to maintain high NOx detection accuracy even when oxygen of high concentration is present in the measurement-object gas.

The present invention includes the following aspects.

(1) A sensor element for detecting NOx in a measurement-object gas, the sensor element comprising:

a base part in an elongated plate shape, including a plurality of oxygen-ion-conductive solid electrolyte layers stacked;

a measurement-object gas flow part for introduction and flow of a measurement-object gas through a gas inlet formed in one end part in a longitudinal direction of the base part;

an inner oxygen pump electrode disposed on an inner surface of the measurement-object gas flow part; and a measurement electrode disposed on the inner surface of the measurement-object gas flow part, wherein the inner oxygen pump electrode has a predetermined length (L) in the longitudinal direction and includes:

a region (A) including an electrode end close to the gas inlet and having a predetermined length ($L_A$) in the longitudinal direction, and a region (B) including an electrode end far from the gas inlet and having a predetermined length ($L_B$) in the longitudinal direction;

the inner oxygen pump electrode comprises a metal material, the metal material including an activity reducing metal that reduces catalytic activity of decomposing NOx;

a content rate of the activity reducing metal in the metal material in the region (A) is higher than a content rate of the activity reducing metal in the metal material in the region (B); and a ratio ($L_A$/L) of the length ($L_A$) in the longitudinal direction of the region (A) of the inner oxygen pump electrode to the length (L) in the longitudinal direction of the inner oxygen pump electrode is 15% to 90%.

(2) The sensor element according to the above (1), wherein the inner oxygen pump electrode comprises a plurality of electrodes disposed on the inner surface of the measurement-object gas flow part, and the length (L) in the longitudinal direction of the inner oxygen pump electrode is a sum of respective lengths in the longitudinal direction of the plurality of electrodes.

(3) The sensor element according to the above (1) or (2), wherein the inner oxygen pump electrode comprises:

an inner main pump electrode disposed on the inner surface of the measurement-object gas flow section, and an auxiliary pump electrode disposed at a position farther from the gas inlet than the inner main pump electrode on the inner surface of the measurement-object gas flow part, and the length (L) in the longitudinal direction of the inner oxygen pump electrode is a sum ($L_1$+$L_2$) of a length ($L_1$) in the longitudinal direction of the inner main pump electrode and a length ($L_2$) in the longitudinal direction of the auxiliary pump electrode.

(4) The sensor element according to the above (3), wherein the auxiliary pump electrode and the measurement electrode are disposed in this order in series in the longitudinal direction at positions farther from the gas inlet than the inner main pump electrode on the inner surface of the measurement-object gas flow part.

(5) The sensor element according to the above (3), wherein the auxiliary pump electrode and the measurement electrode are disposed in parallel in the longitudinal direction at positions farther from the gas inlet than the inner main pump electrode on the inner surface of the measurement-object gas flow part.

(6) The sensor element according to any one of the above (1) to (5), wherein a ratio ($L_A$/L) of the length ($L_A$) in the longitudinal direction of the region (A) of the inner oxygen pump electrode to the length (L) in the longitudinal direction of the inner oxygen pump electrode is 30% to 70%.

(7) The sensor element according to any one of the above (1) to (6), wherein the activity reducing metal comprises at least one selected from the group consisting of gold and silver.

(8) The sensor element according to any one of the above (1) to (7), wherein a content rate of the activity reducing metal in the metal material in the region (A) of the inner oxygen pump electrode is 0.5% by weight to 2.0% by weight.

(9) The sensor element according to any one of the above (1) to (8), wherein a content rate of the activity reducing metal in the metal material in the region (B) of the inner oxygen pump electrode is 0.1% by weight to 0.5% by weight, provided that the content rate of the activity reducing metal in the metal material in the region (B) is lower than a content rate of the activity reducing metal in the metal material in the region (A).

(10) The sensor element according to any one of the above (1) to (9), wherein a ratio ($C_A$/$C_B$) of a content rate ($C_A$) of the activity reducing metal in the metal material in the region (A) to a content rate ($C_B$) of the activity reducing metal in the metal material in the region (B) of the inner oxygen pump electrode is not less than 1.5 and not more than 20.0.

(11) A gas sensor for detecting NOx in a measurement-object gas, comprising the sensor element according to any one of the above (1) to (10).

Advantageous Effect of the Invention

According to the present invention, even when oxygen of high concentration is present in the measurement-object gas, decomposition of NOx can be greatly suppressed in the inner oxygen pump electrode (for example, inner main pump electrode), and thus high NOx detection accuracy can be maintained. That is, it is possible to maintain high NOx detection accuracy regardless of the oxygen concentration in the measurement-object gas.

BRIEF DESCRIPTION OF THE DRAWINGS

FIG. 2 is a schematic view showing a general planar arrangement of an inner main pump electrode 22, an auxiliary pump electrode 51, and a measurement electrode 44 in the sensor element 101. $L_1$ indicates the length of the inner main pump electrode 22 in the longitudinal direction of the sensor element 101, and $L_2$ indicates the length of the auxiliary pump electrode 51 in the longitudinal direction of the sensor element 101. Also, the lower part of FIG. 2 is an image chart of oxygen concentration distribution in the longitudinal direction of the sensor element 101 when a measurement-object gas containing high concentration of oxygen is introduced into the measurement-object gas flow part 15.

FIG. 4 is a schematic view showing a general arrangement of an inner main pump electrode 22 and a measurement electrode 44 in the sensor element 201. $L_1$ indicates the length of the inner main pump electrode 22 in the longitudinal direction of the sensor element 201. Also, the lower part of FIG. 4 is an image chart of oxygen concentration distribution in the longitudinal direction of the sensor element 201 when a measurement-object gas containing high concentration of oxygen is introduced into the measurement-object gas flow part.

FIG. 6 is a schematic view showing a general planar arrangement of an inner main pump electrode 22, an auxiliary pump electrode 51, and a measurement electrode 44 in the sensor element 301. $L_1$ indicates the length of the inner main pump electrode 22 in the longitudinal direction of the sensor element 301, and $L_2$ indicates the length of the auxiliary pump electrode 51 in the longitudinal direction of the sensor element 301. $L_M$ indicates the length of the measurement electrode 44 in the longitudinal direction of the sensor element 301. Also, the lower part of FIG. 6 is an image chart of oxygen concentration distribution in the longitudinal direction of the sensor element 301 when a measurement-object gas containing high concentration of oxygen is introduced into the measurement-object gas flow part.

FIG. 7 is a schematic view showing a general planar arrangement of an inner main pump electrode 22, an auxiliary pump electrode 51, a second auxiliary pump electrode 53, and the measurement electrode 44 in the sensor element 401. $L_1$ indicates the length of the inner main pump electrode 22 in the longitudinal direction of the sensor element 401, and $L_2$ indicates the length of the auxiliary pump electrode 51 in the longitudinal direction of the sensor element 401. $L_3$ indicates the length of the second auxiliary pump electrode 53 in the longitudinal direction of the sensor element 401.

MODES FOR CARRYING OUT OF THE INVENTION

A sensor element of the present invention includes:

a base part in an elongated plate shape, including a plurality of oxygen-ion-conductive solid electrolyte layers stacked;

a measurement-object gas flow part for introduction and flow of a measurement-object gas through a gas inlet formed in one end part in a longitudinal direction of the base part;

an inner oxygen pump electrode disposed on an inner surface of the measurement-object gas flow part; and a measurement electrode disposed on the inner surface of the measurement-object gas flow part, wherein the inner oxygen pump electrode has a predetermined length (L) in the longitudinal direction and includes:

a region (A) including an electrode end close to the gas inlet and having a predetermined length ($L_A$) in the longitudinal direction, and a region (B) including an electrode end far from the gas inlet and having a predetermined length ($L_B$) in the longitudinal direction;

the inner oxygen pump electrode comprises a metal material, the metal material including an activity reducing metal that reduces catalytic activity of decomposing NOx;

a content rate of the activity reducing metal in the metal material in the region (A) is higher than a content rate of the activity reducing metal in the metal material in the region (B); and a ratio ($L_A$/L) of the length ($L_A$) in the longitudinal direction of the region (A) of the inner oxygen pump electrode to the length (L) in the longitudinal direction of the inner oxygen pump electrode is 15% to 90%.

At least a part of the inner oxygen pump electrode is disposed at a position closer to the one end in the longitudinal direction of the base part than the measurement electrode.

By using the gas sensor including the sensor element of the present invention, it is possible to detect NOx in the measurement-object gas.

[General Configuration of Gas Sensor]

Figure 1:
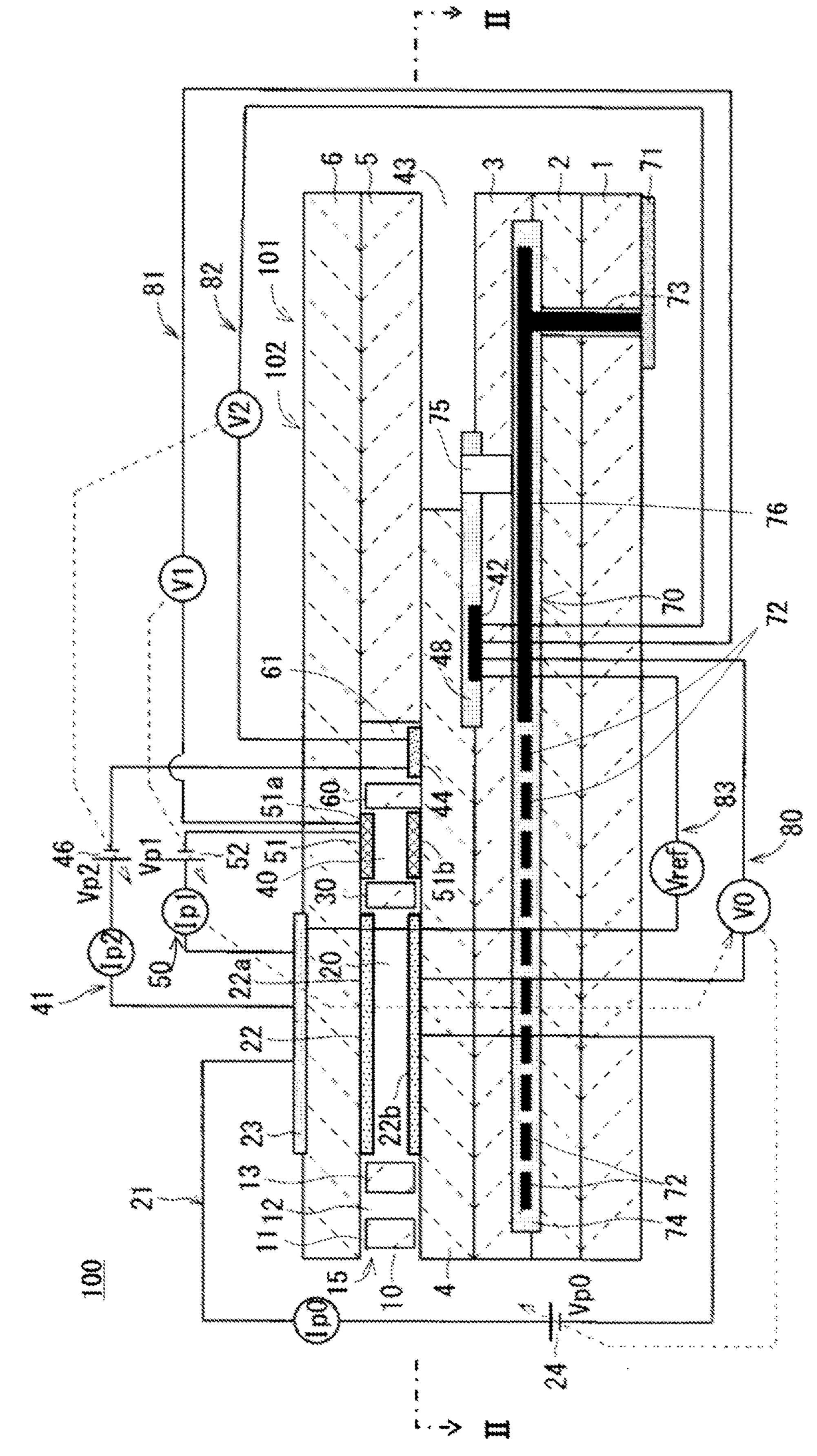
FIG. 1 is a vertical sectional schematic view in a longitudinal direction of a sensor element 101, showing one example of a general configuration of a gas sensor 100.

The sensor element of the present invention will now be described with reference to the drawings. FIG. 1 is a vertical sectional schematic view in the longitudinal direction, showing one example of a general configuration of a gas sensor 100 including a sensor element 101. Hereinafter, based on FIG. 1, the upper side and the lower side in FIG. 1 are respectively defined as top and bottom, and the left side and the right side in FIG. 1 are respectively defined as a front end side and a rear end side.

In the embodiment of FIG. 1, the gas sensor 100 represents one example of a limiting current type NOx sensor that detects NOx in a measurement-object gas by the sensor element 101, and measures the concentration of NOx.

The sensor element 101 is an element in an elongated plate shape, including a base part 102 having such a structure that a plurality of oxygen-ion-conductive solid electrolyte layers are layered. The elongated plate shape also called a long plate shape or a belt shape. The base part 102 has such a structure that six layers, namely, a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO_2$). The solid electrolyte forming these six layers is dense and gastight. These six layers all may have the same thickness, or the thickness may vary among the layers. The layers are adhered to each other with an adhesive layer of a solid electrolyte interposed therebetween, and the base part 102 includes the adhesive layer. While a layer configuration composed of the six layers is illustrated in FIG. 1, the layer configuration in the present invention is not limited to this, and any number of layers and any layer configuration are possible.

The sensor element 101 is manufactured, for example, by stacking ceramic green sheets corresponding to the individual layers after conducting predetermined processing, printing of circuit pattern and the like, and then firing the stacked ceramic green sheets so that they are combined together.

A gas inlet 10 is formed between the lower surface of the second solid electrolyte layer 6 and the upper surface of the first solid electrolyte layer 4 in one end part in the longitudinal direction (hereinafter, referred to as a front end part) of the sensor element 101. A measurement-object gas flow part 15 is formed in such a form that a first diffusion-rate limiting part 11, a buffer space 12, a second diffusion-rate limiting part 13, a first internal cavity 20, a third diffusion-rate limiting part 30, a second internal cavity 40, a fourth diffusion-rate limiting part 60, and a third internal cavity 61 communicate in this order in the longitudinal direction from the gas inlet 10.

The gas inlet 10, the buffer space 12, the first internal cavity 20, the second internal cavity 40, and the third internal cavity 61 constitute an internal space of the sensor element 101. The internal space is provided in such a manner that a portion of the spacer layer 5 is hollowed out, and the top of the internal space is defined by the lower surface of the second solid electrolyte layer 6, the bottom of the internal space is defined by the upper surface of the first solid electrolyte layer 4, and the lateral surface of the internal space is defined by the lateral surface of the spacer layer 5.

Each of the first diffusion-rate limiting part 11, the second diffusion-rate limiting part 13, and the third diffusion-rate limiting part 30 is provided as two laterally elongated slits (having the longitudinal direction of the openings in the direction perpendicular to the figure in FIG. 1). Each of the first diffusion-rate limiting part 11, the second diffusion-rate limiting part 13, and the third diffusion-rate limiting part 30 may be in such a form that a desired diffusion resistance is created, but the form is not limited to the slits.

The fourth diffusion-rate limiting part 60 is provided as a single laterally elongated slit (having the longitudinal direction of the opening in the direction perpendicular to the figure in FIG. 1) between the spacer layer 5 and the second solid electrolyte layer 6. The fourth diffusion-rate limiting part 60 may be in such a form that a desired diffusion resistance is created, but the form is not limited to the slits.

Also, at a position farther from the front end than the measurement-object gas flow part 15, a reference gas introduction space 43 is disposed between the upper surface of the third substrate layer 3 and the lower surface of the spacer layer 5 at a position where the reference gas introduction space 43 is laterally defined by the lateral surface of the first solid electrolyte layer 4. The reference gas introduction space 43 has an opening in the other end part (hereinafter, referred to as a rear end part) of the sensor element 101. As a reference gas for NOx concentration measurement, for example, air is introduced into the reference gas introduction space 43.

An air introduction layer 48 is a layer formed of porous alumina, and is so configured that a reference gas is introduced into the air introduction layer 48 via the reference gas introduction space 43. The air introduction layer 48 is formed to cover a reference electrode 42.

The reference electrode 42 is an electrode sandwiched between the upper surface of the third substrate layer 3 and the first solid electrolyte layer 4, and as described above, the air introduction layer 48 leading to the reference gas introduction space 43 is disposed around the reference electrode 42. That is, the reference electrode 42 is disposed to be in contact with a reference gas via the air introduction layer 48 which is a porous material, and the reference gas introduction space 43. As will be described later, the reference electrode 42 can be used to measure the oxygen concentration (oxygen partial pressure) in the first internal cavity 20, the second internal cavity 40, and the third internal cavity 61.

In the measurement-object gas flow part 15, the gas inlet 10 is open to the external space, and the measurement-object gas is taken into the sensor element 101 from the external space through the gas inlet 10.

In the present embodiment, the measurement-object gas flow part 15 is in such a form that the measurement-object gas is introduced through the gas inlet 10 that is open on the front end surface of the sensor element 101, however, the present invention is not limited to this form. For example, the measurement-object gas flow part 15 need not have a recess of the gas inlet 10. In this case, the first diffusion-rate limiting part 11 substantially serves as a gas inlet.

For example, the measurement-object gas flow part 15 may have an opening that communicates with the buffer space 12 or a position in the vicinity of the buffer space 12 of the first internal cavity 20, on a lateral surface along the longitudinal direction of the base part 102. In this case, the measurement-object gas is introduced from the lateral surface along the longitudinal direction of the base part 102 through the opening.

Further, for example, the measurement-object gas flow part 15 may be so configured that the measurement-object gas is introduced through a porous body.

The first diffusion-rate limiting part 11 creates a predetermined diffusion resistance to the measurement-object gas taken through the gas inlet 10.

The buffer space 12 is provided to guide the measurement-object gas introduced from the first diffusion-rate limiting part 11 to the second diffusion-rate limiting part 13.

The second diffusion-rate limiting part 13 creates a predetermined diffusion resistance to the measurement-object gas introduced into the first internal cavity 20 from the buffer space 12.

It suffices that the amount of the measurement-object gas to be introduced into the first internal cavity 20 falls within a predetermined range. That is, it suffices that a predetermined diffusion resistance is created in a whole from the front end part of the sensor element 101 to the second diffusion-rate limiting part 13. For example, the first diffusion-rate limiting part 11 may directly communicate with the first internal cavity 20, or the buffer space 12 and the second diffusion-rate limiting part 13 may be absent.

The buffer space 12 is provided to mitigate the influence of pressure fluctuation on the detected value when the pressure of the measurement-object gas fluctuates.

When the measurement-object gas is introduced from outside the sensor element 101 into the first internal cavity 20, the measurement-object gas, which is rapidly taken through the gas inlet 10 into the sensor element 101 due to pressure fluctuation of the measurement-object gas in the external space (pulsations in exhaust pressure if the measurement-object gas is automotive exhaust gas), is not directly introduced into the first internal cavity 20. Rather, the measurement-object gas is introduced into the first internal cavity 20 after the pressure fluctuation of the measurement-object gas is eliminated through the first diffusion-rate limiting part 11, the buffer space 12, and the second diffusion-rate limiting part 13. Thus, the pressure fluctuation of the measurement-object gas introduced into the first internal cavity 20 becomes almost negligible.

Figure 2:
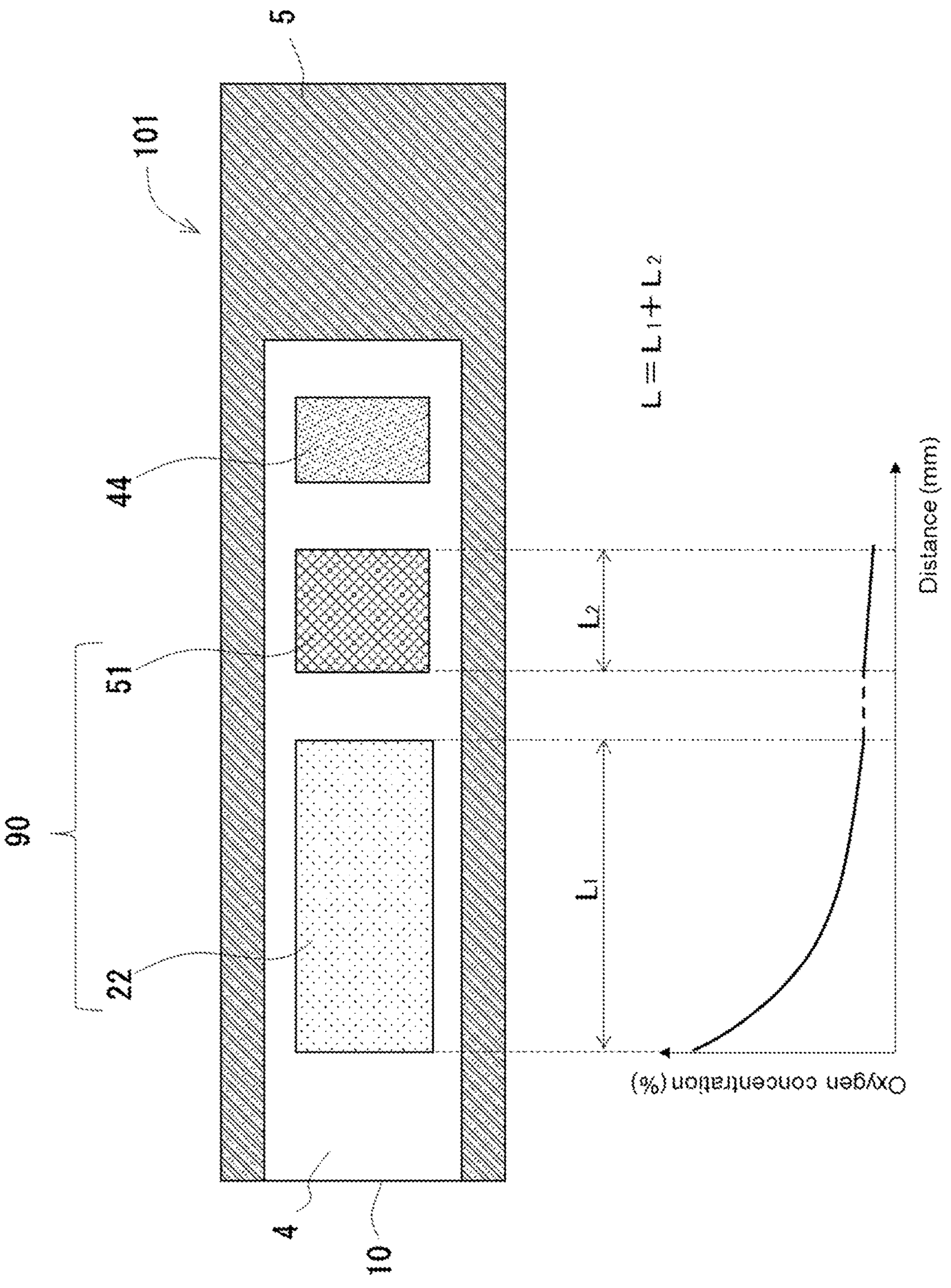
FIG. 2 is a sectional schematic view showing a part of the section along line II-II in FIG. 1.

FIG. 2 is a sectional schematic view showing a part of the section along line II-II in FIG. 1. Referring to FIG. 1 and FIG. 2, an inner oxygen pump electrode 90 is disposed on the inner surface of the measurement-object gas flow part 15, and has a predetermined length (L) in the longitudinal direction of the sensor element 101. The inner oxygen pump electrode 90 comes into contact with the measurement-object gas introduced into the measurement-object gas flow part 15, and contributes to adjusting the oxygen concentration (oxygen partial pressure) in the measurement-object gas to such a level that does not substantially affect measurement of NOx by a measurement electrode 44 described later.

In the sensor element 101 of the present embodiment, the inner oxygen pump electrode 90 includes an inner main pump electrode 22 and an auxiliary pump electrode 51.

That is, in the sensor element 101 of the present embodiment, the inner oxygen pump electrode 90 is divided into the inner main pump electrode 22 and the auxiliary pump electrode 51.

At least a part of the inner oxygen pump electrode 90 is disposed at a position closer to the front end part of the base part 102 than the measurement electrode 44. In the sensor element 101 of the present embodiment, both of the inner main pump electrode 22 and the auxiliary pump electrode 51 are disposed at positions closer to the front end part of the base part 102 than the measurement electrode 44. As in the later-described Variation 2, the inner main pump electrode 22 is disposed at a position closer to the front end part of the base part 102 than the measurement electrode 44, and the auxiliary pump electrode 51 may be disposed in parallel with the measurement electrode 44 in the longitudinal direction of the base part 102.

The first internal cavity 20 is provided as a space for adjusting the oxygen partial pressure in the measurement-object gas introduced through the second diffusion-rate limiting part 13. The oxygen partial pressure is adjusted by operation of a main pump cell 21.

The main pump cell 21 is an electrochemical pump cell including the inner main pump electrode 22 disposed on the inner surface of the measurement-object gas flow part 15, and an outer pump electrode 23 disposed on the outer surface of the base part 102 such that the outer pump electrode 23 and the inner main pump electrode 22 are provided with the second solid electrolyte layer 6 being interposed therebetween.

That is, the main pump cell 21 is an electrochemical pump cell composed of the inner main pump electrode 22 having a ceiling electrode portion **22*a* disposed over substantially the entire surface of the lower surface of the second solid electrolyte layer 6 that faces the first internal cavity 20, the outer pump electrode 23 disposed on a region of the upper surface of the second solid electrolyte layer 6 that corresponds to the ceiling electrode portion 22*a* so as to be exposed to the external space, and the second solid electrolyte layer 6 sandwiched between the inner main pump electrode 22 and the outer pump electrode 23**.

The inner main pump electrode 22 is formed to span the upper and lower solid electrolyte layers (the second solid electrolyte layer 6 and the first solid electrolyte layer 4) that define the first internal cavity 20 and the spacer layer 5 that defines the lateral wall. Specifically, the ceiling electrode portion **22*a* is formed on the lower surface of the second solid electrolyte layer 6 that defines the ceiling surface of the first internal cavity 20, and a bottom electrode portion 22*b* is formed on the upper surface of the first solid electrolyte layer 4 that defines the bottom surface of the first internal cavity 20. Also, lateral electrode portions (not shown) are formed on the lateral wall surfaces (inner surface) of the spacer layer 5 that form both lateral wall parts of the first internal cavity 20 so as to connect the ceiling electrode portion 22*a* and the bottom electrode portion 22*b*. Thus, the inner main pump electrode 22** is provided as a tunnel-like structure in the area where the lateral electrode portions are disposed.

The inner main pump electrode 22 and the outer pump electrode 23 are formed as porous cermet electrodes (the electrode in a state that metal components and ceramic components are mixed).

The main pump cell 21 is configured to be able to adjust the oxygen concentration in the measurement-object gas having flowed into the measurement-object gas flow part 15 to a predetermined concentration. Therefore, it is preferred that the inner main pump electrode 22 which is to come into contact with the measurement-object gas decompose only oxygen without reducing (decomposing) NOx components in the measurement-object gas. Specific electrode structures and constituting materials of the inner oxygen pump electrode 90 (the inner main pump electrode 22 and the auxiliary pump electrode 51 in the sensor element 101 of the present embodiment) will be described later.

In the main pump cell 21, a desired pump voltage Vp0 is applied between the inner main pump electrode 22 and the outer pump electrode 23 by a variable power supply 24 to flow a pump current Ip0 between the inner main pump electrode 22 and the outer pump electrode 23 in either a positive or negative direction, and thus it is possible to pump out oxygen in the first internal cavity 20 to the external space or pump oxygen into the first internal cavity 20 from the external space.

To detect the oxygen concentration (oxygen partial pressure) in the atmosphere in the first internal cavity 20, the inner main pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be detected from an electromotive force V0 measured in the oxygen-partial-pressure detection sensor cell 80 for main pump control. In addition, the pump current Ip0 is controlled by performing feedback control of the pump voltage Vp0 so that the electromotive force V0 is constant. Thus, the oxygen concentration in the first internal cavity 20 can be maintained at a predetermined constant value.

The third diffusion-rate limiting part 30 creates a predetermined diffusion resistance to the measurement-object gas whose oxygen concentration (oxygen partial pressure) has been controlled in the first internal cavity 20 by the operation of the main pump cell 21 and guides the measurement-object gas into the second internal cavity 40.

The second internal cavity 40 is provided as a space for adjusting the oxygen partial pressure in the measurement-object gas introduced through the third diffusion-rate limiting part 30 more accurately. The oxygen partial pressure is adjusted by operation of an auxiliary pump cell 50.

After the oxygen concentration (oxygen partial pressure) in the measurement-object gas is adjusted in advance in the first internal cavity 20, the measurement-object gas is introduced through the third diffusion-rate limiting part 30, and is further subjected to adjustment of the oxygen partial pressure by the auxiliary pump cell 50 in the second internal cavity 40. Thus, the oxygen concentration in the second internal cavity 40 can be kept constant with high accuracy, and the NOx concentration can be measured with high accuracy in the gas sensor 100.

The auxiliary pump cell 50 is an electrochemical pump cell including the auxiliary pump electrode 51 disposed at a position farther from the gas inlet 10 than the inner main pump electrode 22 on the inner surface of the measurement-object gas flow part 15, and the outer pump electrode 23 disposed on the outer surface of the base part 102 such that the outer pump electrode 23 and the auxiliary pump electrode 51 are provided with the second solid electrolyte layer 6 being interposed therebetween.

That is, the auxiliary pump cell 50 is an auxiliary electrochemical pump cell composed of the auxiliary pump electrode 51 having a ceiling electrode portion 51*a* disposed on substantially the entire surface of lower surface of the second solid electrolyte layer 6 facing with the second internal cavity 40, the outer pump electrode 23 (the outer electrode is not limited to the outer pump electrode 23, but may be any suitable electrode outside the sensor element 101), and the second solid electrolyte layer 6.

This auxiliary pump electrode 51 is disposed in the second internal cavity 40 in a tunnel-like structure similar to the inner main pump electrode 22 disposed in the first internal cavity 20. Specifically, in the tunnel-like structure, the ceiling electrode portion 51*a* is formed on the second solid electrolyte layer 6 that defines the ceiling surface of the second internal cavity 40, a bottom electrode portion 51*b* is formed on the first solid electrolyte layer 4 that defines the bottom surface of the second internal cavity 40, and lateral electrode portions (not shown) connecting the ceiling electrode portion 51*a* and the bottom electrode portion 51*b* are formed on the wall surfaces of the spacer layer 5 that define the lateral walls of the second internal cavity 40.

It is preferred that the auxiliary pump electrode 51 be also configured to decompose only oxygen without reducing (decomposing) NOx components in the measurement-object gas as with the case of the inner main pump electrode 22. Specific electrode structures and constituting materials of the inner oxygen pump electrode 90 (the inner main pump electrode 22 and the auxiliary pump electrode 51 in the sensor element 101 of the present embodiment) will be described later.

In the auxiliary pump cell 50, by applying a desired voltage Vp1 between the auxiliary pump electrode 51 and the outer pump electrode 23, it is possible to pump out oxygen in the atmosphere in the second internal cavity 40 to the external space, or pump the oxygen into the second internal cavity 40 from the external space.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, namely, an oxygen-partial-pressure detection sensor cell 81 for auxiliary pump control.

The auxiliary pump cell 50 performs pumping with a variable power supply 52 whose voltage is controlled on the basis of an electromotive force V1 detected by the oxygen-partial-pressure detection sensor cell 81 for auxiliary pump control. Thus, the oxygen partial pressure in the atmosphere in the second internal cavity 40 is controlled to such a low partial pressure that does not substantially affect measurement of NOx.

In addition, a pump current Ip1 is used for control of the electromotive force V0 of the oxygen-partial-pressure detection sensor cell 80 for main pump control. Specifically, the pump current Ip1 is input to the oxygen-partial-pressure detection sensor cell 80 for main pump control as a control signal to control the electromotive force V0, and thus the gradient of the oxygen partial pressure in the measurement-object gas introduced into the second internal cavity 40 from the third diffusion-rate limiting part 30 is controlled to remain constant. In using as a NOx sensor, the oxygen concentration in the second internal cavity 40 is kept at a constant value of about 0.001 ppm by the actions of the main pump cell 21 and the auxiliary pump cell 50.

The fourth diffusion-rate limiting part 60 creates a predetermined diffusion resistance to the measurement-object gas whose oxygen concentration (oxygen partial pressure) has been controlled to further low in the second internal cavity 40 by the operation of the auxiliary pump cell 50, and guides the measurement-object gas into the third internal cavity 61.

The third internal cavity 61 is provided as a space for measuring nitrogen oxide (NOx) concentration in the measurement-object gas introduced through the fourth diffusion-rate limiting part 60. By the operation of a measurement pump cell 41, NOx concentration is measured.

The measurement pump cell 41 is an electrochemical pump cell including a measurement electrode 44 disposed at a position farther from the gas inlet 10 than the auxiliary pump electrode 51 on the inner surface of the measurement-object gas flow part 15, and the outer pump electrode 23 disposed on the outer surface of the base part 102 such that the outer pump electrode 23 and the measurement electrode 44 are provided with the second solid electrolyte layer 6, the spacer layer 5 and the first solid electrolyte layer 4 being interposed therebetween.

That is, the measurement pump cell 41 measures NOx concentration in the measurement-object gas in the third internal cavity 61. The measurement pump cell 41 is an electrochemical pump cell composed of the measurement electrode 44 disposed on the upper surface of the first solid electrolyte layer 4 facing with the third internal cavity 61, the outer pump electrode 23 (the outer electrode is not limited to the outer pump electrode 23, but may be any suitable electrode outside the sensor element 101), the second solid electrolyte layer 6, the spacer layer 5, and the first solid electrolyte layer 4.

The measurement electrode 44 is a porous cermet electrode likewise each of the electrodes 22, 23 and 51. The measurement electrode 44 functions also as a NOx reduction catalyst that reduces NOx present in the atmosphere in the third internal cavity 61.

As a metal material of the measurement electrode 44, a noble metal material having a catalytic activity of decomposing NOx (reducing NOx) may be used. For example, platinum (Pt), rhodium (Rh) or the like may be used. For example, Pt may be used, or an alloy of Pt and Rh may be used. For example, when an alloy of Pt and Rh is used, Rh may be 10% by weight to 90% by weight in amount, relative to the total amount of Pt and Rh.

In the measurement pump cell 41, oxygen generated by decomposition of nitrogen oxide in the atmosphere around the measurement electrode 44 is pumped out, and the amount of generated oxygen can be detected as a pump current Ip2.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an electrochemical sensor cell, namely an oxygen-partial-pressure detection sensor cell 82 for measurement pump control. A variable power supply 46 is controlled on the basis of an electromotive force V2 detected by the oxygen-partial-pressure detection sensor cell 82 for measurement pump control.

The measurement-object gas introduced into the second internal cavity 40 reaches the measurement electrode 44 in the third internal cavity 61 through the fourth diffusion-rate limiting part 60 under the condition that the oxygen partial pressure is controlled. Nitrogen oxide in the measurement-object gas around the measurement electrode 44 is reduced ($2NO \rightarrow N_2+O_2$) to generate oxygen. The generated oxygen is to be pumped by the measurement pump cell 41, and at this time, a voltage Vp2 of the variable power supply 46 is controlled so that the electromotive force V2 detected by the oxygen-partial-pressure detection sensor cell 82 for measurement pump control is constant. Since the amount of oxygen generated around the measurement electrode 44 is proportional to the concentration of nitrogen oxide in the measurement-object gas, nitrogen oxide concentration in the measurement-object gas is calculated by using the pump current Ip2 in the measurement pump cell 41.

By configuring oxygen partial pressure detecting means by an electrochemical sensor cell composed of a combination of the measurement electrode 44, the first solid electrolyte layer 4, the third substrate layer 3 and the reference electrode 42, it is possible to detect an electromotive force in accordance with a difference between the amount of oxygen generated by reduction of NOx components in the atmosphere around the measurement electrode 44 and the amount of oxygen contained in the reference air, and hence it is possible to determine the concentration of NOx components in the measurement-object gas.

Also, the second solid electrolyte layer 6, the spacer layer 5, the first solid electrolyte layer 4, the third substrate layer 3, the outer pump electrode 23, and the reference electrode 42 constitute an electrochemical sensor cell 83, and it is possible to detect the oxygen partial pressure in the measurement-object gas outside the sensor by an electromotive force Vref obtained by the sensor cell 83.

In the gas sensor 100 having such a configuration, the main pump cell 21 and the auxiliary pump cell 50 are operated to supply a measurement-object gas whose oxygen partial pressure is usually kept at a low constant value (the value that does not substantially affect measurement of NOx) to the measurement pump cell 41. Therefore, NOx concentration in the measurement-object gas can be detected on the basis of the pump current Ip2 that flows as a result of pumping out of the oxygen generated by reduction of NOx by the measurement pump cell 41 and is almost in proportion to the concentration of NOx in the measurement-object gas.

The sensor element 101 further includes a heater part 70 that functions as a temperature regulator of heating and maintaining the temperature of the sensor element 101 so as to enhance the oxygen ion conductivity of the solid electrolyte. The heater part 70 includes a heater electrode 71, a heater 72, a heater lead 76, a through hole 73, a heater insulating layer 74, and a pressure relief vent 75.

In the sensor element 101 of the present embodiment, the heater part 70 is embedded in the base part 102, but this form is not limitative. In the sensor element 101, heating may be conducted to develop oxygen ion conductivity with which the main pump cell 21, the auxiliary pump cell 50, and the measurement pump cell 41 are operable. The heater part 70 may be formed as a member separated from the sensor element 101, or heating may be conducted by a measurement-object gas at high temperature. For accurate measurement, it is preferred that the temperature of the sensor element 101 be constant regardless of the temperature of the measurement-object gas. In consideration of this point, it is preferred that the sensor element 101 include the heater part 70 as in the present embodiment.

The heater electrode 71 is an electrode formed in contact with the lower surface of the first substrate layer 1. The power can be supplied to the heater part 70 from the outside by connecting the heater electrode 71 with a heater power supply that is an external power supply.

The heater 72 is an electrical resistor sandwiched by the second substrate layer 2 and the third substrate layer 3 from top and bottom. The heater 72 is connected with the heater electrode 71 via a heater lead 76 that connects with the heater 72 and extends in the rear end side in the longitudinal direction of the sensor element 101, and the through hole 73. The heater 72 is externally powered through the heater electrode 71 to generate heat, and heats and maintains the temperature of the solid electrolyte forming the sensor element 101.

The heater 72 is embedded over the whole area from the first internal cavity 20 to the third internal cavity 61 so that the temperature of the entire sensor element 101 can be adjusted to such a temperature that activates the solid electrolyte. The temperature may be adjusted so that the main pump cell 21, the auxiliary pump cell 50, and the measurement pump cell 41 are operable. It is not necessary that the whole area is adjusted to the same temperature, but the sensor element 101 may have temperature distribution.

In the sensor element 101 of the present embodiment, the heater 72 is embedded in the base part 102, but this form is not limitative. The heater 72 may be disposed to heat the base part 102. That is, the heater 72 may heat the sensor element 101 to develop oxygen ion conductivity with which the main pump cell 21, the auxiliary pump cell 50, and the measurement pump cell 41 are operable. For example, the heater 72 may be embedded in the base part 102 as in the present embodiment. Alternatively, for example, the heater part 70 may be formed as a heater substrate that is separate from the base part 102, and may be disposed at a position adjacent to the base part 102.

A heater insulating layer 74 is formed of an insulator such as alumina on the upper and lower surfaces of the heater 72 and the heater lead 76. The heater insulating layer 74 is formed to ensure electrical insulation between the second substrate layer 2, and the heater 72 and the heater lead 76, and electrical insulation between the third substrate layer 3, and the heater 72 and the heater lead 76.

The pressure relief vent 75 extends through the third substrate layer 3 so that the heater insulating layer 74 and the reference gas introduction space 43 communicate with each other. The pressure relief vent 75 can mitigate an increase in internal pressure due to temperature rise in the heater insulating layer 74. The pressure relief vent 75 may be absent.

(Inner Oxygen Pump Electrode)

As described above, it is preferred that the inner oxygen pump electrode 90 (the inner main pump electrode 22 and the auxiliary pump electrode 51 in the sensor element 101 of the present embodiment) be configured to decompose only oxygen without reducing (decomposing) NOx components in the measurement-object gas. In such a configuration, NOx is not decomposed in the inner oxygen pump electrode 90, and all the NOx in the measurement-object gas reaches the measurement electrode 44, and thus it is possible to detect NOx with high accuracy in the measurement pump cell 41.

The main pump cell 21 discharges oxygen from the first internal cavity 20 so that the oxygen concentration in the first internal cavity 20 is a predetermined constant value. The higher the oxygen concentration in the measurement-object gas, the larger the amount of oxygen to be discharged. That is, the pump current Ip0 in the main pump cell 21 increases. Since the applied voltage Vp0 in the main pump cell 21 is substantially in proportion to the pump current Ip0, the higher the oxygen concentration in the measurement-object gas, the larger the applied voltage Vp0.

If the applied voltage Vp0 is too high, NOx may be decomposed in the inner main pump electrode 22. This leads to reduction in the amount of NOx reaching the measurement electrode 44. As a result, the current value Ip2 detected by the measurement pump cell 41 is smaller than the value that is to be originally detected. Especially when oxygen concentration of the measurement-object gas is high, the detection accuracy of NOx may decrease.

Figure 3:
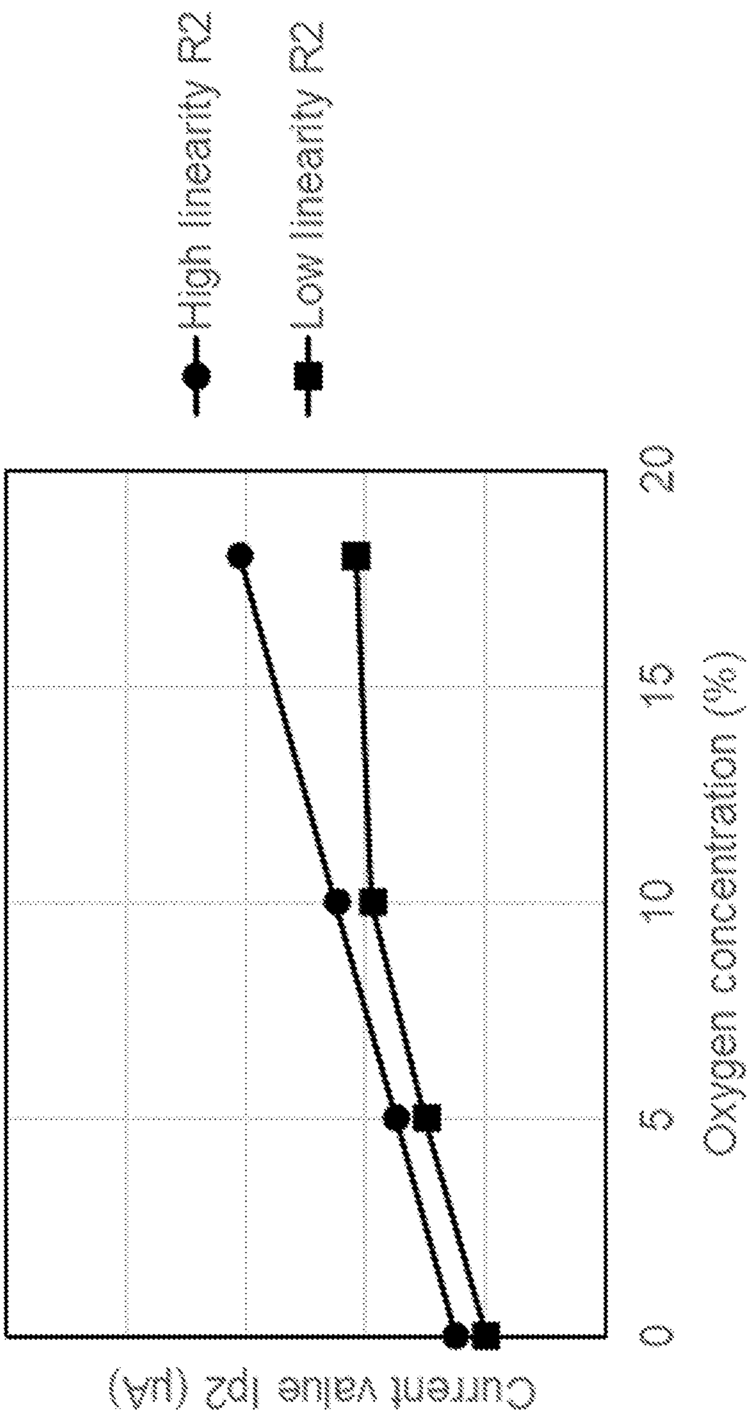
FIG. 3 is a schematic diagram showing the relation between the oxygen concentration and the NOx output current value Ip2 in the presence of oxygen ($O_2$=0, 5, 10, 18%).

The NOx output current value Ip2 is described for the case where the detection accuracy of NOx does not decrease under the high oxygen concentration, and where the detection accuracy of NOx decreases. FIG. 3 is a schematic diagram showing the relation between the oxygen concentration and the NOx output current value Ip2 in the presence of oxygen ($O_2$=0, 5, 10, 18%). Concentration of each gas component is indicated on a volume basis.

As an index of whether or not the detection accuracy of NOx is kept high under high oxygen concentration, a coefficient of determination $R^2$ in a linear regression equation between plural oxygen concentrations and the respective Ip2 values at the respective oxygen concentrations can be used. The coefficient of determination $R^2$ is called linearity $R^2$ of NOx output.

In FIG. 3, the black circle "●" schematically indicates a NOx output current value Ip2 in a gas sensor capable of measuring with high accuracy even at high oxygen concentration, namely, a gas sensor having high linearity $R^2$ of NOx output. The black square "■" schematically shows a NOx output current value Ip2 in a gas sensor having low detection accuracy of NOx at high oxygen concentration, namely, a gas sensor having low linearity $R^2$ of NOx output.

The higher the linearity $R^2$ of NOx output, namely, the closer to 1 the linearity $R^2$ is, with the higher accuracy NOx can be detected regardless of the oxygen concentration in the measurement-object gas. The linearity $R^2$ of NOx output may be, for example, 0.900 or more. It is expected that NOx can be measured with high accuracy in actual use by using such a gas sensor. More preferably, the linearity $R^2$ of NOx output may be 0.950 or more. Further preferably, the linearity $R^2$ of NOx output may be 0.975 or more.

The linearity $R^2$ of NOx output can be calculated, for example, by using a model gas. Four kinds of model gas each having a constant NOx concentration of 500 ppm and an oxygen concentration of 0, 5, 10, or 18% may be subjected to measurement by the gas sensor 100. A coefficient of determination $R^2$ may be calculated in the linear regression equation between respective oxygen concentrations of model gas, and the measured four NOx output current values Ip2. The model gas is not limited to these four kinds, but may be appropriately selected depending on the use modes that are assumed for the gas sensor 100.

Decrease in NOx detection accuracy under high oxygen concentration is studied in more detail. FIG. 2 is a sectional schematic view showing a part of the section along line II-II in FIG. 1. FIG. 2 is a schematic view showing a general planar arrangement of the inner main pump electrode 22, the auxiliary pump electrode 51, and the measurement electrode 44 disposed on the upper surface of the first solid electrolyte layer 4. $L_1$ indicates the length of the inner main pump electrode 22 in the longitudinal direction of the sensor element 101, and $L_2$ indicates the length of the auxiliary pump electrode 51 in the longitudinal direction of the sensor element 101. From each electrode toward the rear end of the element, an electrode lead (not shown) is disposed to allow connection with the outside. The spacer layer 5 that forms the lower surface of the fourth diffusion-rate limiting part 60 is omitted in the drawing.

Also shown in the lower part of FIG. 2 is an image chart of oxygen concentration distribution in the longitudinal direction of the sensor element 101 when a measurement-object gas containing high concentration of oxygen is introduced into the measurement-object gas flow part 15.

Referring to FIG. 1 and FIG. 2, the operation of the main pump cell 21 when a measurement-object gas having high oxygen concentration is introduced into the first internal cavity 20 is considered. The following consideration can be made. When the measurement-object gas is introduced into the first internal cavity 20, most of oxygen in the measurement-object gas is discharged by the main pump cell 21. The inner main pump electrode 22 has a predetermined length ($L_1$) in the longitudinal direction of the sensor element 101. Referring to the image chart of oxygen concentration distribution in the longitudinal direction of the sensor element 101 in FIG. 2, it is considered that more oxygen is discharged at a position close to the gas inlet 10 in the inner main pump electrode 22. Namely, in the microscopic view, it is considered that the discharge amount of oxygen varies depending on the position in the inner main pump electrode 22. As a result, in the microscopic view, it is considered that a local pump current value Ip0 (local) varies depending on the position in the inner main pump electrode 22.

At a position close to the gas inlet 10 in the inner main pump electrode 22, it is necessary to discharge more oxygen, so that it is assumed that the local applied voltage Vp0 (local) at that position is high. Accordingly, when NOx decomposes in the inner main pump electrode 22 under high oxygen concentration, it is assumed that the NOx is decomposed at a position close to the gas inlet 10 in the inner main pump electrode 22.

From the above, it is expected that decomposition of NOx in the inner main pump electrode 22 under high oxygen concentration can be effectively suppressed by using a material whose catalytic activity of decomposing NOx is further reduced especially at a position close to the gas inlet 10 in the inner main pump electrode 22.

The details of the inner oxygen pump electrode 90 (the inner main pump electrode 22 and the auxiliary pump electrode 51 in the sensor element 101 of the present embodiment) are described below.

(Shape of Inner Oxygen Pump Electrode)

In the sensor element 101 of the present embodiment, each of the inner main pump electrode 22 and the auxiliary pump electrode 51 is substantially rectangular. The shape of the electrode is not limited to a rectangular shape, and may be appropriately determined by a person skilled in the art.

The inner oxygen pump electrode 90 has a predetermined length (L) in the longitudinal direction of the base part 102. In the sensor element 101 of the present embodiment, the inner main pump electrode 22 has a predetermined length ($L_1$) in the longitudinal direction of the sensor element 101, and the auxiliary pump electrode 51 has a predetermined length ($L_2$) in the longitudinal direction of the sensor element 101. The length (L) of the inner oxygen pump electrode 90 is the sum ($L=L_1+L_2$) of the length ($L_1$) of the inner main pump electrode 22 and the length ($L_2$) of the auxiliary pump electrode 51.

The size of the inner main pump electrode 22 may be appropriately determined by a person skilled in the art. The inner main pump electrode 22 may have such a size that the main pump cell 21 can keep the oxygen concentration in the first internal cavity 20 at a predetermined constant value. For example, the length ($L_1$) of the inner main pump electrode 22 in the longitudinal direction of the sensor element 101 may be 2.0 mm to 7.0 mm. The width of the inner main pump electrode 22 in the direction perpendicular to the longitudinal direction of the sensor element 101 may be 1.0 mm to 4.0 mm. The thickness of the inner main pump electrode 22 may be 5.0 μm to 30.0 μm.

The inner main pump electrode 22 may be formed on the lower surface of the second solid electrolyte layer 6 facing with the first internal cavity 20. Also, as described above, the inner main pump electrode 22 may have the ceiling electrode portion 22*a* and the bottom electrode portion 22*b*. Each of the ceiling electrode portion 22*a* and the bottom electrode portion 22*b* may have the size described above. In the sensor element 101 of the present embodiment, the ceiling electrode portion 22*a* and the bottom electrode portion 22*b* have the same shape. In the configuration having the ceiling electrode portion 22*a* and the bottom electrode portion 22*b*, it is expected that the oxygen concentration in the first internal cavity 20 can be controlled with higher accuracy since the electrode area can be made large relative to the volume of the first internal cavity 20.

The size of the auxiliary pump electrode 51 may be appropriately determined by a person skilled in the art. The auxiliary pump electrode 51 may have such a size that the auxiliary pump cell 50 can control the oxygen partial pressure in the atmosphere in the second internal cavity 40 to such a low partial pressure that does not substantially affect measurement of NOx. Typically, the auxiliary pump electrode 51 may be smaller than the inner main pump electrode 22. For example, the length ($L_2$) of the auxiliary pump electrode 51 in the longitudinal direction of the sensor element 101 may be 1.0 mm to 2.5 mm. The width of the auxiliary pump electrode 51 in the direction perpendicular to the longitudinal direction of the sensor element 101 may be 0.3 mm to 2.5 mm. The thickness of the auxiliary pump electrode 51 may be 5.0 μm to 30.0 μm.

The auxiliary pump electrode 51 may be formed on the lower surface of the second solid electrolyte layer 6 facing with the second internal cavity 40. Also, as described above, the auxiliary pump electrode 51 may have the ceiling electrode portion 51*a* and the bottom electrode portion 51*b*. Each of the ceiling electrode portion 51*a* a and the bottom electrode portion 51*b* may have the size described above. In the sensor element 101 of the present embodiment, the ceiling electrode portion 51*a* and the bottom electrode portion 51*b* have the same shape. In the configuration having the ceiling electrode portion 51*a* and the bottom electrode portion 51*b*, it is expected that the oxygen concentration in the second internal cavity 40 can be controlled with higher accuracy since the electrode area can be made large relative to the volume of the second internal cavity 40.

(Constituting Material of Inner Oxygen Pump Electrode)

The inner oxygen pump electrode 90 (namely, the inner main pump electrode 22 and the auxiliary pump electrode 51) is each a porous cermet electrode (electrode in a form in which a metal component and a ceramic component are mixed) as described above. The ceramic component is not particularly limited, but an oxygen ion conductive solid electrolyte is preferably used as well as used in the base part 102. For example, as the ceramic component, $ZrO_2$ can be used. The metal component and the ceramic component in the porous cermet electrode may be appropriately determined by a person skilled in the art. For example, an amount of the ceramic component can be about 30% by weight to 50% by weight in the total of the metal component and the ceramic component. For example, when Pt is used as the metal component, and $ZrO_2$ is used as the ceramic component, the weight ratio of Pt:$ZrO_2$ may roughly be 7.0:3.0 to 5.0:5.0.

Hereinafter, metal materials in the inner main pump electrode 22 and the auxiliary pump electrode 51 will be specifically described.

(Metal Material of Inner Oxygen Pump Electrode)

As described above, the main pump cell 21 is configured to be able to adjust the oxygen concentration in the measurement-object gas having flowed into the measurement-object gas flow part 15 to a predetermined concentration. Therefore, it is preferred that the inner main pump electrode 22 that is to come into contact with the measurement-object gas decompose only oxygen without reducing (decomposing) NOx components in the measurement-object gas.

For example, as a metal material of the inner main pump electrode 22, a material based on a metal having a catalytic activity of decomposing oxygen to which a metal that reduces a catalytic activity of decomposing the target gas to be measured (hereinafter, referred to as an activity reducing metal) is added may be used. Examples of the metal having a catalytic activity of decomposing oxygen include platinum (Pt).

Platinum (Pt) is a material that is widely used as a catalyst in general applications as well as in the field of gas sensor. Pt has a catalytic activity for oxygen, and a catalytic activity of decomposing the target gas to be measured (for example, NOx). By adding the activity reducing metal that reduces the catalytic activity of decomposing NOx to such Pt, it is expected that the catalytic activity of decomposing NOx can be reduced while the catalytic activity to oxygen is maintained.

Examples of the metal that reduces the catalytic activity of decomposing NOx include gold (Au) and silver (Ag). It is considered that these activity reducing metals do not have catalytic activity of decomposing NOx. Preferably, gold (Au) can be used.

(Composition of Metal Material in Inner Oxygen Pump Electrode)

The inner oxygen pump electrode 90 includes:

a region (A) including an electrode end close to the gas inlet 10 (namely, close to the front end part of the base part 102) and having a predetermined length ($L_A$) in a longitudinal direction of the base part 102, and a region (B) including an electrode end far from the gas inlet 10 (namely, far from the front end part of the base part 102) and having a predetermined length ($L_B$) in the longitudinal direction, and a content rate of an activity reducing metal in a metal material in the region (A) is higher than a content rate of the activity reducing metal in the metal material in the region (B).

The region (B) of the inner oxygen pump electrode 90 may be the entire region other than the region (A) of the inner oxygen pump electrode 90. That is, the inner oxygen pump electrode 90 may be composed of the region (A) having a high content rate of the activity reducing metal in the metal material, and the region (B) having a low content rate of the activity reducing metal in the metal material.

In the sensor element 101 of the present embodiment, as described above, the inner oxygen pump electrode 90 includes:

the inner main pump electrode 22 having a predetermined length ($L_1$) in the longitudinal direction of the sensor element 101, and the auxiliary pump electrode 51 having a predetermined length ($L_2$) in the longitudinal direction of the sensor element 101.

In the sensor element 101 of the present embodiment, the inner main pump electrode 22 and the auxiliary pump electrode 51 include:

a region (A) including an electrode end of the inner main pump electrode 22 close to the gas inlet 10 and having a predetermined length ($L_A$) in a longitudinal direction of the base part 102, and a region (B) including an electrode end of the auxiliary pump electrode 51 far from the gas inlet 10 and having a predetermined length ($L_B$) in the longitudinal direction, and a content rate of an activity reducing metal in a metal material in the region (A) is higher than a content rate of the activity reducing metal in the metal material in the region (B).

A ratio ($L_A$/L) of the length ($L_A$) of the region (A) of the inner oxygen pump electrode 90 in a longitudinal direction of the sensor element 101 to the length (L) of the inner oxygen pump electrode 90 in the longitudinal direction is not less than 15% and not more than 90%. More preferably, the ratio ($L_A$/L) may be not less than 30% and not more than 70%.

By configuring the region (A) to satisfy the above range, it is expected that decomposition of NOx in the inner main pump electrode 22 under high oxygen concentration can be effectively suppressed.

Also by configuring the region (A) to satisfy the above range, it is expected that NOx detection sensitivity can be maintained even after use of the gas sensor for a long term under high oxygen concentration in a high temperature range.

Specifically, when the gas sensor is used for a long term under high oxygen concentration in a high temperature range, it is assumed that the activity reducing metal in the inner main pump electrode 22 and the auxiliary pump electrode 51 evaporates and the evaporated activity reducing metal adheres to the measurement electrode 44. When the activity reducing metal adheres to the measurement electrode 44, NOx decomposition performance in the measurement electrode 44 deteriorates. As a result, it is considered that not all of NOx in the measurement-object gas having reached the measurement electrode 44 can be decomposed, and the NOx detection current value Ip2 is smaller than the actual value. In other words, NOx detection sensitivity deteriorates by the use of the gas sensor.

However, by configuring the region (A) to satisfy the above range, even when the activity reducing metal in the inner main pump electrode 22 and the auxiliary pump electrode 51 evaporates due to a long term use of the gas sensor, the amount of the activity reducing metal adhering to the measurement electrode 44 can be suppressed. That is, it is expected that change with time in NOx sensitivity after use of the gas sensor for a long time can be suppressed.

In the sensor element 101 of the present embodiment, the length (L) of the inner oxygen pump electrode 90 is the sum ($L=L_1+L_2$) of the length ($L_1$) of the inner main pump electrode 22 and the length ($L_2$) of the auxiliary pump electrode 51. That is, the ratio ($L_A$/L) in the sensor element 101 is a ratio [$L_A/(L_1+L_2)$] of $L_A$ to $L_1+L_2$.

When $L_A$ is smaller than $L_1$ ($L_A<L_1$):

the activity reducing metal is contained much in a region of the inner main pump electrode 22, having a length of $L_A$ in the longitudinal direction of the sensor element 101 from the electrode end close to the gas inlet 10.

When $L_A$ is equal to $L_1$ ($L_A=L_1$):

the activity reducing metal is contained much in the entire inner main pump electrode 22 (length: $L_1=L_A$).

When $L_A$ is larger than $L_1$ ($L_A>L_1$):

the activity reducing metal is contained much in the entire inner main pump electrode 22 (length: $L_1$), and in a region of the auxiliary pump electrode 51, having a length of $L_A-L_1$ in the longitudinal direction of the sensor element 101 from the electrode end close to the gas inlet 10.

The content rate of the activity reducing metal in each of the metal material in the region (A) and the region (B) of the inner oxygen pump electrode 90 can be appropriately set as long as decomposition of NOx under high oxygen concentration in the inner main pump electrode 22 can be suppressed. This is based on the premise that the content rate in the region (A) is higher than the content rate in the region (B).

For example, when gold (Au) is added as the activity reducing metal to platinum (Pt) which is the main component, the content rate (concentration) of Au in the region (A) containing much Au may be not less than 0.5% by weight and not more than 2.0% by weight, relative to the total amount of the metal material. Preferably, the content rate may be not less than 0.7% by weight and not more than 2.0% by weight. More preferably, the content rate may be not less than 1.5% by weight and not more than 2.0% by weight. By satisfying such a range, it is expected that decomposition of NOx in the inner main pump electrode 22 under high oxygen concentration can be effectively suppressed.

The content rate (concentration) of Au in the region (B) in the inner main pump electrode 22 and the auxiliary pump electrode 51 may be not less than 0.1% by weight and not more than 0.5% by weight, relative to the total amount of the metal material. Preferably, the content rate may be not less than 0.1% by weight and not more than 0.4% by weight. More preferably, the content rate may be not less than 0.1% by weight and not more than 0.3% by weight. It is expected that by employing such a range, the amount of Au evaporating from the inner main pump electrode 22 and the auxiliary pump electrode 51 can be reduced, and as a result, the amount of Au adhering to the measurement electrode 44 can be suppressed, even after a long-term use of the gas sensor. Therefore, it is expected that deterioration in NOx detection sensitivity can be suppressed.

An Au content rate ratio ($C_A/C_B$) of a content rate ($C_A$) of Au in the region (A) having a high content rate of the activity reducing metal to a content rate ($C_B$) of Au in the region (B) having a low content rate may be not less than 1.5 and not more than 20.0.

By making the Au content rate ratio ($C_A/C_B$) satisfy such a range, it is expected that decomposition of NOx of the inner main pump electrode 22 can be effectively suppressed especially on the front end side of the sensor element 101, under high oxygen concentration. Also it is expected to be able to reduce the amount of Au that evaporates from the inner main pump electrode 22 and the auxiliary pump electrode 51 and adheres to the measurement electrode 44.

That is, it is expected that by selecting the Au content rate ratio ($C_A/C_B$) in such a range, both of the two effects described above can be achieved. As a result, it is possible to maintain high NOx detection accuracy regardless of the oxygen concentration in the measurement-object gas.

The inner oxygen pump electrode 90 (the inner main pump electrode 22 and the auxiliary pump electrode 51) may be configured by two regions having different Au content rates, namely, the region (A) and the region (B) respectively having a high content rate and a low content rate of the activity reducing metal in the metal material as described above.

Alternatively, the inner oxygen pump electrode 90 may be configured by three or more regions having different Au content rates that decrease stepwise in the longitudinal direction from the side close to the front end part of the sensor element 101. In other words, the inner oxygen pump electrode 90 may be configured by the region (A) including two or more regions having different Au concentrations, and the region (B) having a constant Au concentration. That is, the content rate of the activity reducing metal in the metal material may decrease stepwise from the part close to the gas inlet 10 toward the part far from the gas inlet 10 of the inner oxygen pump electrode 90 in the longitudinal direction of the sensor element 101.

Also, the inner oxygen pump electrode 90 may have a concentration gradient in the longitudinal direction of the sensor element 101. That is, the content rate of the activity reducing metal in the metal material may decrease continuously from the part close to the gas inlet 10 toward the part far from the gas inlet 10 of the region (A) in the longitudinal direction of the sensor element 101.

Also when Ag or the like is used as the activity reducing metal, the content rate of Au, and the configuration of the region (A) and the region (B) in the inner oxygen pump electrode 90 described above can be referenced.

By employing the configuration of the inner oxygen pump electrode 90 as described above, it is expected that decomposition of NOx in the inner main pump electrode 22 under high oxygen concentration can be effectively suppressed. That is, even when the oxygen concentration in the measurement-object gas is high, it is possible to detect NOx with high accuracy. That is, it is possible to maintain high NOx detection accuracy regardless of the oxygen concentration in the measurement-object gas.

By employing the configuration of the inner oxygen pump electrode 90 as described above, even when the gas sensor is used for a long time under high oxygen concentration in a high temperature range, it is expected that the amount of the activity reducing metal evaporating from the inner oxygen pump electrode 90 and adhering to the measurement electrode 44 can be reduced. As a result, it is possible to suppress deterioration in the NOx decomposition performance in the measurement electrode 44 by the use of the gas sensor, and thus it is possible to suppress deterioration in the NOx detection sensitivity. That is, the change with time of the NOx sensitivity can be suppressed. As a result, it is considered that the durability of the gas sensor improves.

Hereinafter, an example of other embodiment of the sensor element of the present invention will be described.

(Variation 1)

Figure 4:
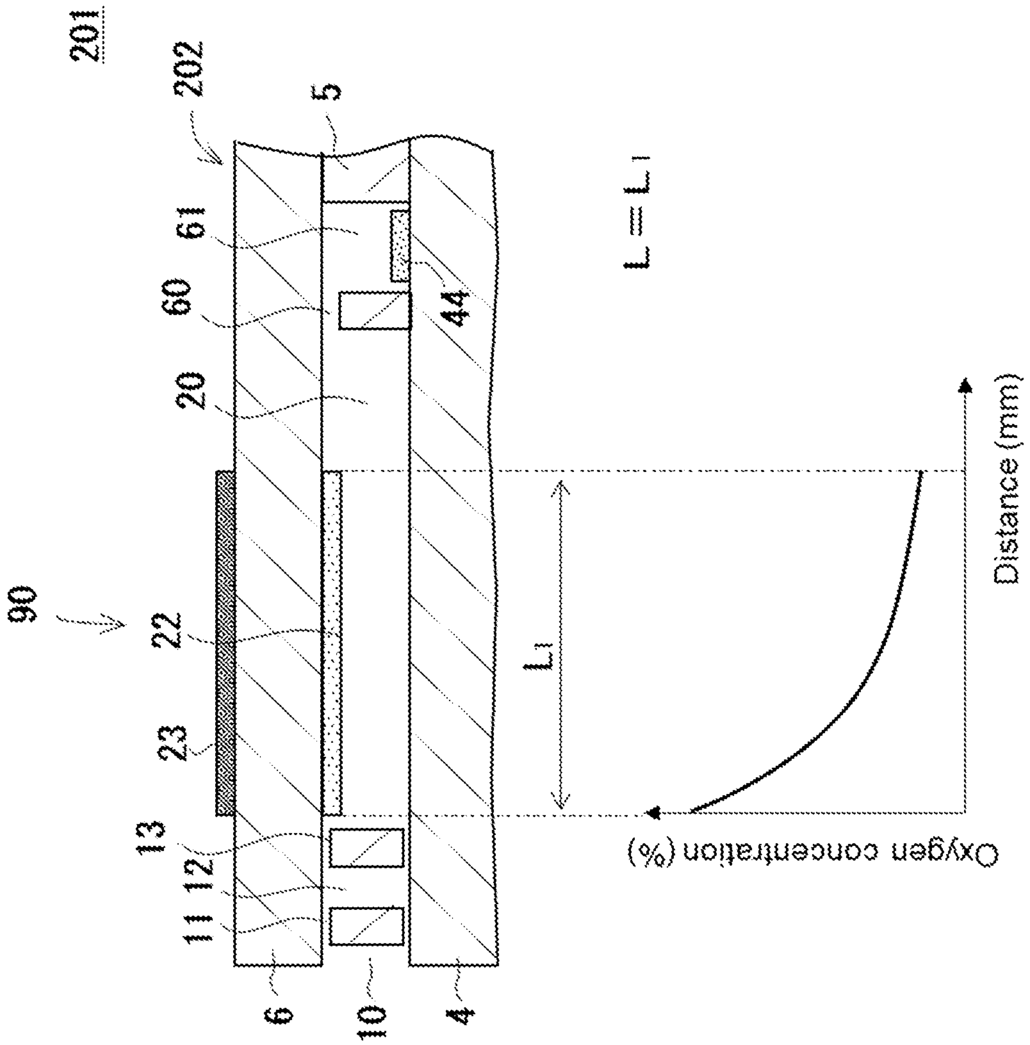
FIG. 4 is a sectional schematic view showing a part of the vertical section in the longitudinal direction of a sensor element 201 of Example.

FIG. 4 is a sectional schematic view showing a part of the vertical section in the longitudinal direction of a sensor element 201 of Variation 1 used in Example. $L_1$ indicates the length of the inner main pump electrode 22 in the longitudinal direction of the sensor element 201. Also shown in the lower part of FIG. 4 is an image chart of oxygen concentration distribution in the longitudinal direction of the sensor element 201 when a measurement-object gas containing high concentration of oxygen is introduced into the measurement-object gas flow part.

The sensor element 201 of Variation 1 is a sensor element having the main pump cell 21 and the measurement pump cell 41. The sensor element 201 of Variation 1 has two internal cavities, namely, the first internal cavity 20 and the third internal cavity 61. The inner main pump electrode 22 constituting a part of the main pump cell 21 is formed on the lower surface of the second solid electrolyte layer 6 facing with the first internal cavity 20. The measurement electrode 44 constituting a part of the measurement pump cell 41 is formed on the upper surface of the first solid electrolyte layer 4 facing with the third internal cavity 61.

The sensor element 201 of Variation 1 adjusts the oxygen concentration in the measurement-object gas introduced into the first internal cavity 20 by the main pump cell 21 to a predetermined constant concentration. Specifically, by controlling the electromotive force V0 in the oxygen-partial-pressure detection sensor cell 80 for main pump control to a constant value corresponding to a predetermined oxygen partial pressure, it is possible to keep the oxygen concentration in the first internal cavity 20 at a predetermined constant value.

In the sensor element 201 of Variation 1, the inner oxygen pump electrode 90 is the inner main pump electrode 22. The length (L) of the inner oxygen pump electrode 90 in the longitudinal direction of the sensor element 201 is equal to the length ($L_1$) of the inner main pump electrode 22 in the longitudinal direction of the sensor element 201 ($L=L_1$).

In the inner main pump electrode 22 of the sensor element 201 of Variation 1, the length ($L_A$) of the region (A) containing much activity reducing metal in the longitudinal direction of the sensor element 201 occupies 15% to 90% of the length ($L_1$) of the inner main pump electrode 22 in the longitudinal direction of the sensor element 201. That is, the ratio ($L_A/L_1$) of $L_A$ to $L_1$ is 15% to 90%. More preferably, the ratio ($L_A/L_1$) of $L_A$ to $L_1$ may be 30 to 70%.

For the configuration other than those described above, the description of the sensor element 101 of the foregoing embodiment can be referenced.

(Variation 2)

Figure 5:
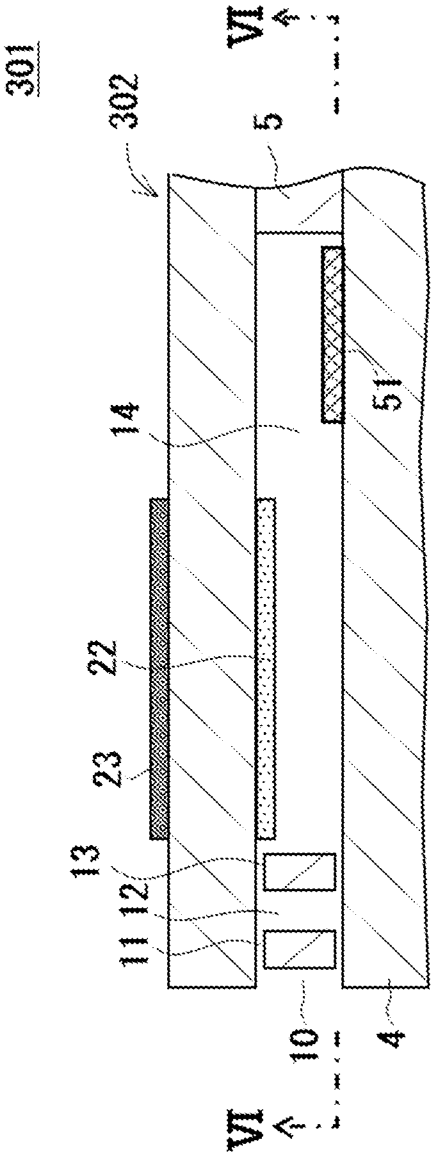
FIG. 5 is a sectional schematic view showing a part of the vertical section in the longitudinal direction of a sensor element 301 of Example.

FIG. 5 is a sectional schematic view showing a part of the vertical section in the longitudinal direction of a sensor element 301 of Variation 2 used in Example.

Figure 6:
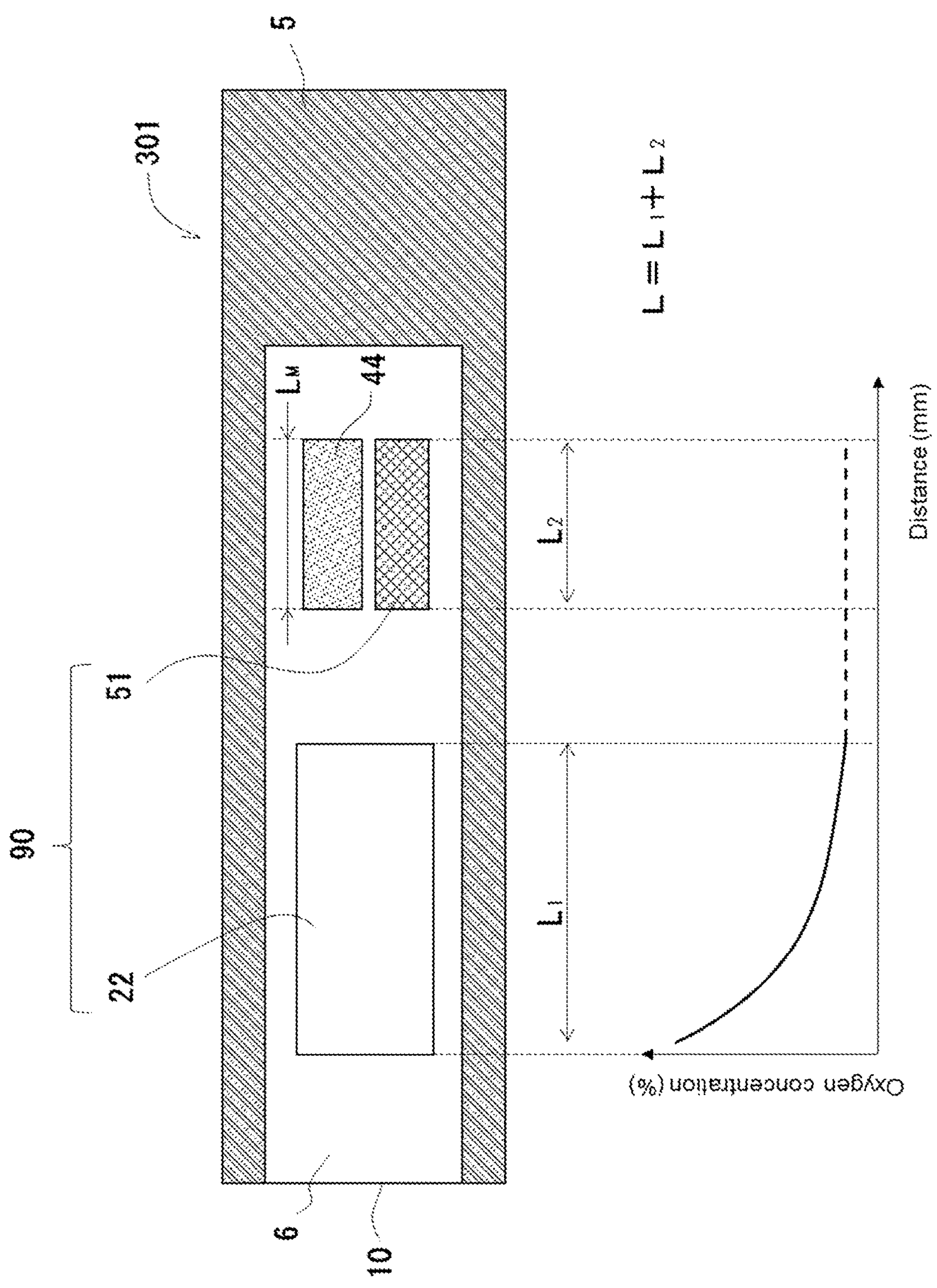
FIG. 6 is a sectional schematic view showing a section along line VI-VI in FIG. 5.

FIG. 6 is a sectional schematic view showing a section along line VI-VI in FIG. 5. FIG. 6 shows a general planar arrangement of the inner main pump electrode 22 disposed on the lower surface of the second solid electrolyte layer 6, and the auxiliary pump electrode 51 and the measurement electrode 44 disposed on the upper surface of the first solid electrolyte layer 4 in the sensor element 301 of Variation 2. From each electrode toward the rear end of the element, an electrode lead (not shown) is disposed to allow connection with the outside. The spacer layer 5 that forms the diffusion-rate limiting parts 11 and 13 is omitted in the drawing.

Also shown in the lower part of FIG. 6 is an image chart of oxygen concentration distribution in the longitudinal direction of the sensor element 301 when a measurement-object gas containing high concentration of oxygen is introduced into the measurement-object gas flow part 15.

In the sensor element 301 of Variation 2, the inner main pump electrode 22 is disposed facing with the one internal cavity 14 close to the front end part of the sensor element 301 on the lower surface of the second solid electrolyte layer 6. Also, the auxiliary pump electrode 51 and the measurement electrode 44 are disposed in parallel in the longitudinal direction of the sensor element 301, on the side closer to the rear end part of the sensor element 301 than the inner main pump electrode 22 on the upper surface of the first solid electrolyte layer 4.

In the sensor element 301 of Variation 2, the inner oxygen pump electrode 90 is divided into the inner main pump electrode 22 and the auxiliary pump electrode 51 as with the case of the sensor element 101. In the sensor element 301 of Variation 2, the length (L) of the inner oxygen pump electrode 90 in the longitudinal direction of the sensor element 301 is the sum of the length ($L_1$) of the inner main pump electrode 22 in the longitudinal direction of the sensor element 301, and the length ($L_2$) of the auxiliary pump electrode 51 in the longitudinal direction of the sensor element 301 ($L=L_1+L_2$).

In the sensor element 301 of Variation 2, the length ($L_2$) of the auxiliary pump electrode 51 in the longitudinal direction of the sensor element 301 may be equivalent to a length ($L_M$) of the measurement electrode 44 in the longitudinal direction of the sensor element 301. For example, $L_2$ may be equal to $L_M$ ($L_2=L_M$), or may roughly satisfy $0.8\times L_M \leq L_2 \leq 1.2\times L_M$. The length ($L_1$) of the inner main pump electrode 22 may be, for example, 1 to 5 folds the length ($L_M$) of the measurement electrode 44. Preferably, the length ($L_1$) may be 2 to 4 folds the length ($L_M$). With such a range, it is possible to adjust the oxygen partial pressure in the measurement-object gas reaching the measurement electrode 44 to a sufficiently low predetermined value.

In the sensor element 301 of Variation 2, the oxygen partial pressure may be adjusted by operating the main pump cell 21 alone. The auxiliary pump electrode 51 may be used as an oxygen sensing electrode for detecting the oxygen partial pressure in the vicinity of the measurement electrode 44 having adjusted by the main pump cell 21. For detection of the oxygen partial pressure, the electromotive force V1 in the oxygen-partial-pressure detection sensor cell 81 for auxiliary pump control may be used, or a current value between the auxiliary pump electrode 51 and the outer pump electrode 23 (or the reference electrode 42) may be used.

For the configuration other than those described above, the description of the sensor element 101 of the foregoing embodiment can be referenced.

(Variation 3)

Figure 7:
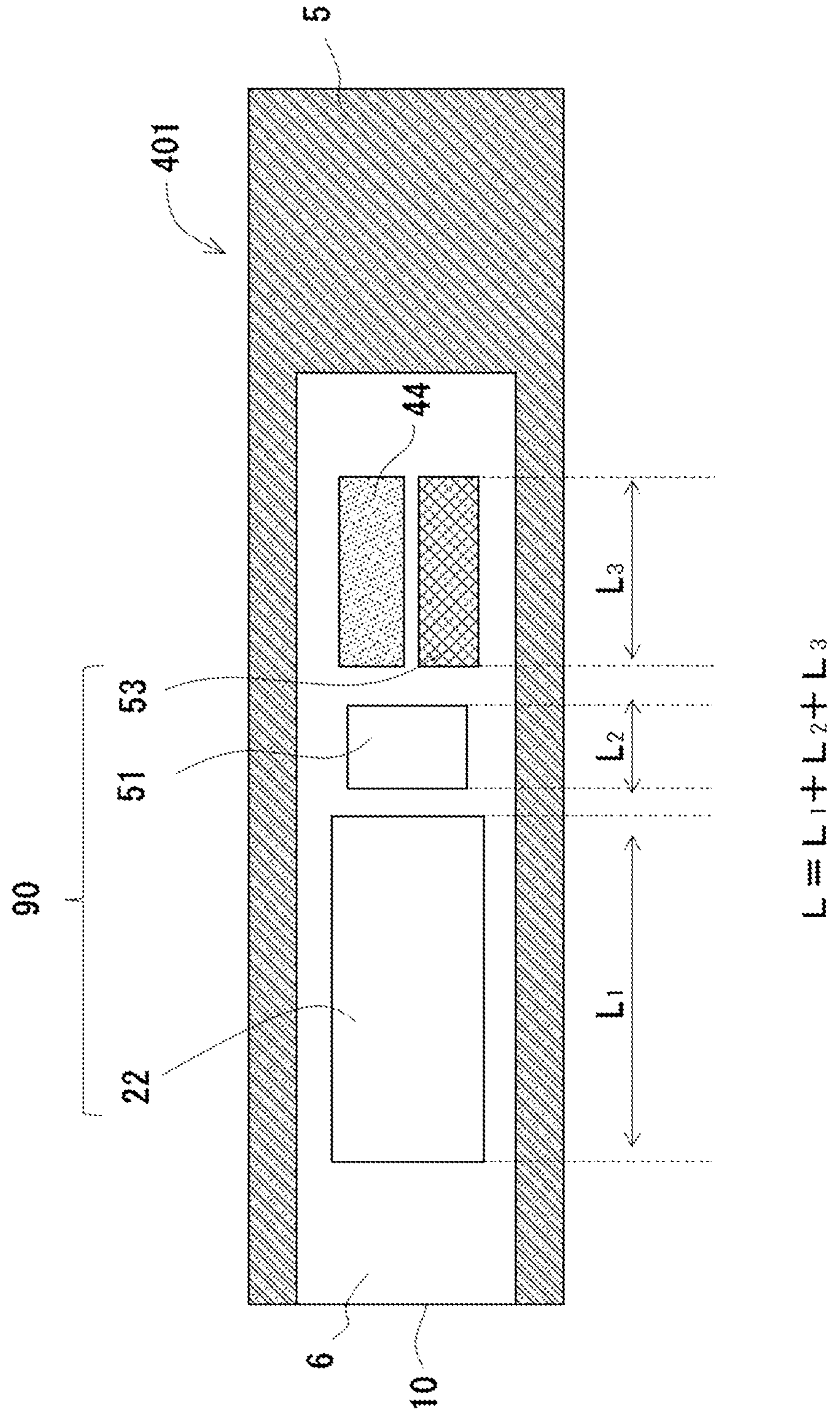
FIG. 7 is a sectional schematic view of a sensor element 401 of a Variation in the same section of FIG. 6.

FIG. 7 is a sectional schematic view of a sensor element 401 of Variation 3 in the same section of FIG. 6. FIG. 7 is a schematic view showing a general planar arrangement of the inner main pump electrode 22 and the auxiliary pump electrode 51 disposed on the lower surface of the second solid electrolyte layer 6, and a second auxiliary pump electrode 53 and the measurement electrode 44 disposed on the upper surface of the first solid electrolyte layer 4 in the sensor element 401.

As illustrated, the second auxiliary pump electrode 53 may further be disposed in parallel with the measurement electrode 44 in addition to the inner main pump electrode 22 and the auxiliary pump electrode 51. In this case, the inner main pump electrode 22 and the auxiliary pump electrode 51 may be used to adjust the oxygen partial pressure in the measurement-object gas. In such a case, the second auxiliary pump electrode 53 may be used as an oxygen sensing electrode for detecting the adjusted oxygen partial pressure in the vicinity of the measurement electrode 44. For detection of the oxygen partial pressure, an electromotive force between the second auxiliary pump electrode 53 and the reference electrode 42 may be used, or a current value between the second auxiliary pump electrode 53 and the outer pump electrode 23 (or the reference electrode 42) may be used.

In the sensor element 401 of Variation 3, the inner oxygen pump electrode 90 is divided into the inner main pump electrode 22, the auxiliary pump electrode 51, and the second auxiliary pump electrode 53. In the sensor element 401 of Variation 3, the length (L) of the inner oxygen pump electrode 90 in the longitudinal direction of the sensor element 401 is the sum of the length ($L_1$) of the inner main pump electrode 22 in the longitudinal direction of the sensor element 401, the length ($L_2$) of the auxiliary pump electrode 51 in the longitudinal direction of the sensor element 401, and the length ($L_3$) of the second auxiliary pump electrode 53 in the longitudinal direction of the sensor element 401 ($L=L_1+L_2+L_3$).

For the total length ($L_1+L_2$) of the length ($L_1$) of the inner main pump electrode 22 and the length ($L_2$) of the auxiliary pump electrode 51 in the sensor element 401 of Variation 3, the relationship between the length ($L_1$) of the inner main pump electrode 22 and the length ($L_M$) of the measurement electrode 44 in the sensor element 301 of Variation 2 can be referenced. For the length $L_3$ of the second auxiliary pump electrode 53 in the sensor element 401 of Variation 3, the relationship between the length ($L_2$) of the auxiliary pump electrode 51 and the length ($L_M$) of the measurement electrode 44 in the sensor element 301 of Variation 2 can be referenced.

For the configuration other than those described above, the description of the sensor element 101 of the foregoing embodiment can be referenced.

While the sensor elements 101, 201, 301, 401 have been indicated as examples of embodiments of the present invention, the present invention is not limited to these embodiments. The present invention can include a sensor element including the inner oxygen pump electrode 90 of various forms as long as the object of the present invention of maintaining high NOx detection accuracy regardless of the oxygen concentration in the measurement-object gas is achieved.

[Method for Producing Sensor Element]

Next, one example of a method for producing the sensor element as described above is described. A plurality of unfired sheet moldings (so-called green sheets) containing an oxygen-ion-conductive solid electrolyte such as zirconia ($ZrO_2$) as a ceramic component are subjected to a predetermined processing and printing of circuit pattern, and then the plurality of sheets are laminated, and the laminate was cut, and then fired. Thus the sensor element 101 can be manufactured.

Hereinafter, description is made while taking the case of manufacturing the sensor element 101 composed of six layers shown in FIG. 1 as an example.

First, six green sheets containing an oxygen-ion-conductive solid electrolyte such as zirconia ($ZrO_2$) as a ceramic component are prepared. For manufacturing of the green sheets, a known molding method can be used. The six green sheets may all have the same thickness, or the thickness differs depending on the layer to be formed. In each of the six green sheets, sheet holes or the like for use in positioning at the time of printing or stacking are formed in advance by a known method such as a punching process with a punching apparatus (blank sheet). In the blank sheet for use as the spacer layer 5, penetrating parts such as internal cavities are also formed in the same manner. Also in the remaining layers, necessary penetrating parts are formed in advance.

The blank sheets for use as six layers, namely, the first substrate layer 1, the second substrate layer 2, the third substrate layer 3, the first solid electrolyte layer 4, the spacer layer 5, and the second solid electrolyte layer 6 are subjected to printing of various patterns required for respective layers and drying treatment. For printing of a pattern, a known screen printing technique can be used. Also as the drying treatment, a known drying means can be used.

For example, the case of manufacturing the sensor element 101 in which the region of the inner main pump electrode 22 from the electrode end close to the gas inlet 10 to the length $L_A$ in the longitudinal direction of the sensor element 101 is the region (A) having a high content rate of the activity reducing metal is considered. In the sensor element 101, the region other than the region (A) of the inner main pump electrode 22, and the auxiliary pump electrode 51 are the region (B) having a low content rate of the activity reducing metal.

In forming the inner main pump electrode 22, an electrode paste for high content rate region (A) and an electrode paste for low content rate region (B), having different content rates of Au in the metal material, are prepared.

Then, the electrode paste for high content rate region (A) is printed and dried on the second solid electrolyte layer 6 in a desired pattern of forming the region (A) of the inner main pump electrode 22. Also, the electrode paste for low content rate region (B) is printed and dried in a desired pattern of forming the region (B) of the inner main pump electrode 22 (namely, the region other than the high concentration region (A)). Also, the electrode paste for low content rate region (B) is printed and dried in a desired pattern of forming the auxiliary pump electrode 51. The order of these printings may be appropriately determined.

After completing the printing and drying of diverse patterns for each of the six blank sheets by repeating these steps, contact bonding treatment of stacking the six printed blank sheets in a predetermined order while positioning with the sheet holes and the like, and contact bonding at a predetermined temperature and pressure condition to give a laminate is conducted. The contact bonding treatment is conducted by heating and pressurizing with a known laminator such as a hydraulic press. While the temperature, the pressure and the time of heating and pressurizing depend on the laminator being used, they may be appropriately determined to achieve excellent lamination.

The obtained laminate includes a plurality of sensor elements 101. The laminate is cut into units of the sensor element 101. The cut laminate is fired at a predetermined firing temperature to obtain the sensor element 101. The firing temperature may be such a temperature that the solid electrolyte forming the base part 102 of the sensor element 101 is sintered to become a dense product, and an electrode or the like maintains desired porosity. The firing is conducted, for example, at a firing temperature of about 1300 to 1500° C.

The obtained sensor element 101 is incorporated into the gas sensor 100 in such a form that the front end part of the sensor element 101 comes into contact with the measurement-object gas, and the rear end part of the sensor element 101 comes into contact with the reference gas.

EXAMPLES

Hereinafter, the case of actually manufacturing a sensor element and conducting a test is described as Examples. The present invention is not limited to the following Examples.

Examples 1 to 16 and Comparative Examples 1 to 2

As Examples 1 to 16 and Comparative Examples 1 to 2, the sensor element 201 of Variation 1 shown in FIG. 4 was manufactured.

As described above, in the sensor element 201 of Variation 1, the inner oxygen pump electrode 90 is the inner main pump electrode 22. The length (L) of the inner oxygen pump electrode 90 in the longitudinal direction of the sensor element 201 is equal to the length ($L_1$) of the inner main pump electrode 22 in the longitudinal direction of the sensor element 201 ($L=L_1$).

The inner main pump electrode 22 is composed of the region (A) including an electrode end close to the front end part of the sensor element 201 and having the length ($L_A$) in the longitudinal direction of the sensor element 201, and the region (B) including an electrode end far from the front end part of the sensor element 201 and having the length ($L_B$) in the longitudinal direction of the sensor element 201. That is, $L_1=L_A+L_B$.

As the metal material of the inner main pump electrode 22, the material based on Pt to which Au is added was used. The region (A) was manufactured to have a higher concentration (content rate) of Au relative to the total amount of Pt and Au than the region (B). Here, the region (A) is called a high concentration region (A). Also, the region (B) is called a low concentration region (B).

As Examples 1 to 16 and Comparative Examples 1 to 2, the sensor element 201 shown in FIG. 4 was manufactured according to the aforementioned production method of the sensor element 101. Table 1 shows a concentration (% by weight) of Au relative to the total amount of Pt and Au in the high concentration region (A); a concentration (% by weight) of Au relative to the total amount of Pt and Au in the low concentration region (B); a ratio ($L_A/L_1$) (%) of the length ($L_A$) of the high concentration region (A) in the longitudinal direction of the sensor element 201 to the total length ($L=L_1$) of the inner oxygen pump electrode 90 (inner main pump electrode 22) in the longitudinal direction of the sensor element 201; and a ratio (Au concentration ratio:

$C_A/C_B$) of Au concentration ($C_A$) in the high concentration region (A) to Au concentration ($C_B$) in the low concentration region (B) in every level.

Specifically, as an electrode paste for the inner main pump electrode 22, electrode pastes having different Au concentrations relative to the total amount of Pt and Au were prepared. The Au concentration relative to the total amount of Pt and Au in each electrode paste was 0.10% by weight, 0.30% by weight, 0.50% by weight, 0.75% by weight, 0.90% by weight, 1.00% by weight, or 2.00% by weight.

The shape of the inner main pump electrode 22 was a rectangle having the length ($L_1$) of 5.0 mm in the longitudinal direction of the sensor element 201, and the width of 2.0 mm perpendicular to the longitudinal direction of the sensor element 201 in every level. In every level, the thickness of the inner main pump electrode 22 was 15 μm.

In each of Examples 1 to 16 and Comparative Examples 1 to 2, an electrode paste having an Au concentration in each level was printed on the high concentration region (A) of ratio ($L_A/L_1$) in each level in the inner main pump electrode 22 as shown in Table 1. An electrode paste having an Au concentration in each level was printed on the low concentration region (B) which is the remaining region in the inner main pump electrode 22.

Except for the above, the sensor elements of Examples 1 to 16 and Comparative Examples 1 to 2 were manufactured according to the aforementioned production method of the sensor element 101. A gas sensor in which the manufactured sensor element was incorporated was manufactured to conduct the later-described judgement test.

[Judgement Test 1]

By measurement using a model gas, the linearity of the NOx detection current Ip2 to the oxygen concentration was obtained. Specifically, the test was conducted in the following manner.

The gas sensor of Example 1 was measured in a model gas device. The gas sensor of Example 1 was attached to a piping for measurement of the model gas device. The gas sensor of Example 1 was driven. A model gas satisfying NO=500 ppm and 02=0% was flowed in the piping for measurement, and Ip2 current value ($Ip2_{(500,0)}$) of the gas sensor in Example 1 was measured. Also for the model gas satisfying NO=500 ppm and 02=5%, the model gas satisfying NO=500 ppm and 02=10%, and the model gas satisfying NO=500 ppm and 02=18%, Ip2 current values ($Ip2_{(500,5)}$, $Ip2_{(500,10)}$, $Ip2_{(500,18)}$) of the gas sensor in Example 1 were measured in the same manner. The gas components other than NO and $O_2$ in the model gas used for measurement were $H_2O$ (3%) and $N_2$ (remainder).

The coefficient of determination $R^2$ was calculated in the linear regression equation between the oxygen concentration of the model gas, and measured four Ip2 values ($Ip2_{(500,0)}$, $Ip2_{(500,5)}$, $Ip2_{(500,10)}$, $Ip2_{(500,18)}$). The coefficient of determination $R^2$ is called linearity of NOx output. For each of Examples 2 to 16 and Comparative Examples 1 to 2, the linearity $R^2$ was calculated in the same manner.

The calculated linearity $R^2$ of NOx output was judged according to the following criteria (Judgement 1).

A: Linearity $R^2$ of NOx output is not less than 0.975

B: Linearity $R^2$ of NOx output is less than 0.975 and not less than 0.950

C: Linearity $R^2$ of NOx output is less than 0.950 and not less than 0.900

D: Linearity $R^2$ of NOx output is less than 0.900

If the judgement is A, B or C, it is considered that NOx can be detected with high accuracy even under high oxygen concentration in actual use. In other words, it is considered that NOx can be detected and/or concentration of NOx can be measured with high accuracy regardless of the oxygen concentration in the measurement-object gas.

[Judgement Test 2]

A durability test using a diesel engine was conducted, and the degree of deterioration in NOx detection sensitivity was evaluated. Before and after the durability test, NOx sensitivity (Ip2 current value) of the gas sensor at a NO concentration of 500 ppm was measured, and a rate of change in NOx sensitivity before and after the durability test was calculated. The degree of deterioration in NOx detection sensitivity was evaluated and judged according to the rate of change in NOx sensitivity. Specifically, the test was conducted in the following manner.

First, the gas sensor of Example 1 was measured in a model gas device. The gas sensor of Example 1 was attached to a piping for measurement of the model gas device. The gas sensor of Example 1 was driven. A model gas satisfying NO=500 ppm and $O_2$=0% was flowed in the piping for measurement, and Ip2 current value ($Ip2_{fresh}$) of the gas sensor in Example 1 was measured. For each of Examples 2 to 16 and Comparative Examples 1 to 2, Ip2 current value ($Ip2_{fresh}$) was measured in the same manner. The gas components other than NO and $O_2$ in the model gas used for measurement were $H_2O$ (3%) and $N_2$ (remainder).

Next, a durability test using a diesel engine was conducted. The gas sensor of each of Examples 1 to 16 and Comparative Examples 1 to 2 was attached to a piping of an exhaust gas pipe of an automobile. Then, the gas sensor of each of Examples 1 to 16 and Comparative Examples 1 to 2 was driven. In this condition, an operation pattern of 40 minutes at an engine speed ranging from 1500 to 3500 rpm, and a load torque ranging from 0 to 350 N·m was repeated until 4000 hours had lapsed. In the operation pattern, the gas temperature was 200° C. to 600° C., and the NOx concentration was 0 to 1500 ppm.

At the point of time after a lapse of 1000 hours from the start of the test, the durability test was suspended, and the gas sensors of Examples 1 to 16 and Comparative Examples 1 to 2 were taken out. For the taken out gas sensors of Examples 1 to 16 and Comparative Examples 1 to 2, Ip2 current value ($Ip2_{aged1000H}$) of each gas sensor in the gas sensor after a lapse of 1000 hours of the durability test was measured in the method described above.

For each of the gas sensors of Examples 1 to 16 and Comparative Examples 1 to 2, the amount of change in the NOx detection sensitivity before and after the durability test was calculated. In other words, a rate of change (rate of change in NOx sensitivity) of the Ip2 current value ($Ip2_{aged1000H}$) after a lapse of 1000 hours of the durability test to the Ip2 current value ($Ip2_{fresh}$) before the durability test was calculated.

$$\text{Rate of change in NOx sensitivity (\%)} = (Ip2_{aged1000H}/IP2_{fresh}-1)\times 100$$

After measuring the Ip2 current value ($Ip2_{aged1000H}$) after a lapse of 1000 hours of the durability test, the gas sensors of Examples 1 to 16 and Comparative Examples 1 to 2 were attached again to the piping of the exhaust gas pipe. Then, the aforementioned durability test using a diesel engine was resumed, and the durability test was continued until the cumulative lapse time had reached 2000 hours.

For each of the gas sensors of Examples 1 to 16 and Comparative Examples 1 to 2 after a lapse of 2000 hours of the durability test, a rate of change (rate of change in NOx sensitivity) of the Ip2 current value ($Ip2_{aged2000H}$) after a lapse of 2000 hours of the durability test to the Ip2 current value ($Ip2_{fresh}$) before the durability test was calculated in the same manner as the case after the lapse of 1000 hours.

In the same manner, a rate of change (rate of change in NOx sensitivity) of the Ip2 current value ($Ip2_{aged3000H}$) after a lapse of 3000 hours of the durability test to the Ip2 current value ($Ip2_{fresh}$) before the durability test, and a rate of change (rate of change in NOx sensitivity) of the Ip2 current value ($Ip2_{aged4000H}$) after a lapse of 4000 hours of the durability test to the Ip2 current value ($Ip2_{fresh}$) before the durability test were calculated.

TABLE 1

| Level | Au concentration [wt. %] in high concentration region (A) | Au concentration [wt. %] in low concentration region (B) | a ratio ($L_A/L_1$) (%) of high concentration region (A) to inner oxygen pump electrode | Au concentration ratio ($C_A/C_B$) | Judgement 1 | Judgement 2 | Rate of change in NOx sensitivity (%) in Judgement test 2 | | | |
|---|---|---|---|---|---|---|---|---|---|---|
| | | | | | | | 1000 hrs | 2000 hrs | 3000 hrs | 4000 hrs |
| Example 1 | 0.75 | 0.50 | 15.0 | 1.5 | C | A | −3.0 | −4.8 | −7.5 | −12.8 |
| Example 2 | 0.75 | 0.50 | 30.0 | 1.5 | B | A | −3.2 | −5.1 | −8.0 | −13.3 |
| Example 3 | 0.75 | 0.50 | 50.0 | 1.5 | A | A | −3.7 | −5.5 | −8.5 | −13.8 |
| Example 4 | 0.75 | 0.50 | 70.0 | 1.5 | A | A | −3.4 | −5.8 | −9.2 | −14.5 |
| Example 5 | 0.75 | 0.50 | 90.0 | 1.5 | A | C | −9.8 | −18.6 | −25.4 | −33.4 |
| Example 6 | 0.90 | 0.30 | 15.0 | 3.0 | B | A | −2.8 | −4.6 | −8.1 | −12.0 |
| Example 7 | 0.90 | 0.30 | 30.0 | 3.0 | A | A | −3.4 | −5.2 | −9.1 | −13.8 |
| Example 8 | 0.90 | 0.30 | 50.0 | 3.0 | A | A | −3.6 | −5.6 | −9.3 | −14.2 |
| Example 9 | 0.90 | 0.30 | 90.0 | 3.0 | A | B | −5.3 | −10.1 | −15.3 | −20.7 |
| Example 10 | 1.00 | 0.10 | 15.0 | 10.0 | A | A | −3.0 | −4.1 | −8.2 | −12.4 |
| Example 11 | 1.00 | 0.10 | 30.0 | 10.0 | A | A | −2.5 | −4.6 | −9.0 | −13.6 |
| Example 12 | 1.00 | 0.10 | 50.0 | 10.0 | A | A | −2.9 | −4.5 | −9.4 | −14.8 |
| Example 13 | 1.00 | 0.10 | 90.0 | 10.0 | A | B | −4.6 | −8.3 | −12.1 | −18.6 |
| Example 14 | 2.00 | 0.10 | 15.0 | 20.0 | A | A | −2.3 | −4.4 | −8.8 | −13.0 |
| Example 15 | 2.00 | 0.10 | 50.0 | 20.0 | A | A | −3.5 | −6.3 | −9.6 | −15.4 |
| Example 16 | 2.00 | 0.10 | 90.0 | 20.0 | A | C | −10.5 | −19.8 | −29.7 | −35.6 |
| Comparative Example 1 | 0.75 | 0.50 | 5.0 | 1.5 | D | A | −2.8 | −4.6 | −6.8 | −11.5 |
| Comparative Example 2 | 0.75 | 0.75 | 100.0 | 1.0 | A | D | −11.1 | −22.5 | −31.2 | −33.5 |

Based on the rate of change in NOx sensitivity (%) after a lapse of 3000 hours of the durability test, judgement was made according to the following criteria (Judgement 2).

A: Rate of change in NOx sensitivity is not more than ±10%

B: Rate of change in NOx sensitivity is more than ±10% and not more than ±20%

C: Rate of change in NOx sensitivity is more than ±20% and not more than ±30%

D: Rate of change in NOx sensitivity is more than ±30%

It is considered that when the judgement is A, B or C after a lapse of 3000 hours of the durability test described above, NOx can be detected with high accuracy even after using for a long term in actual use.

Figure 8:
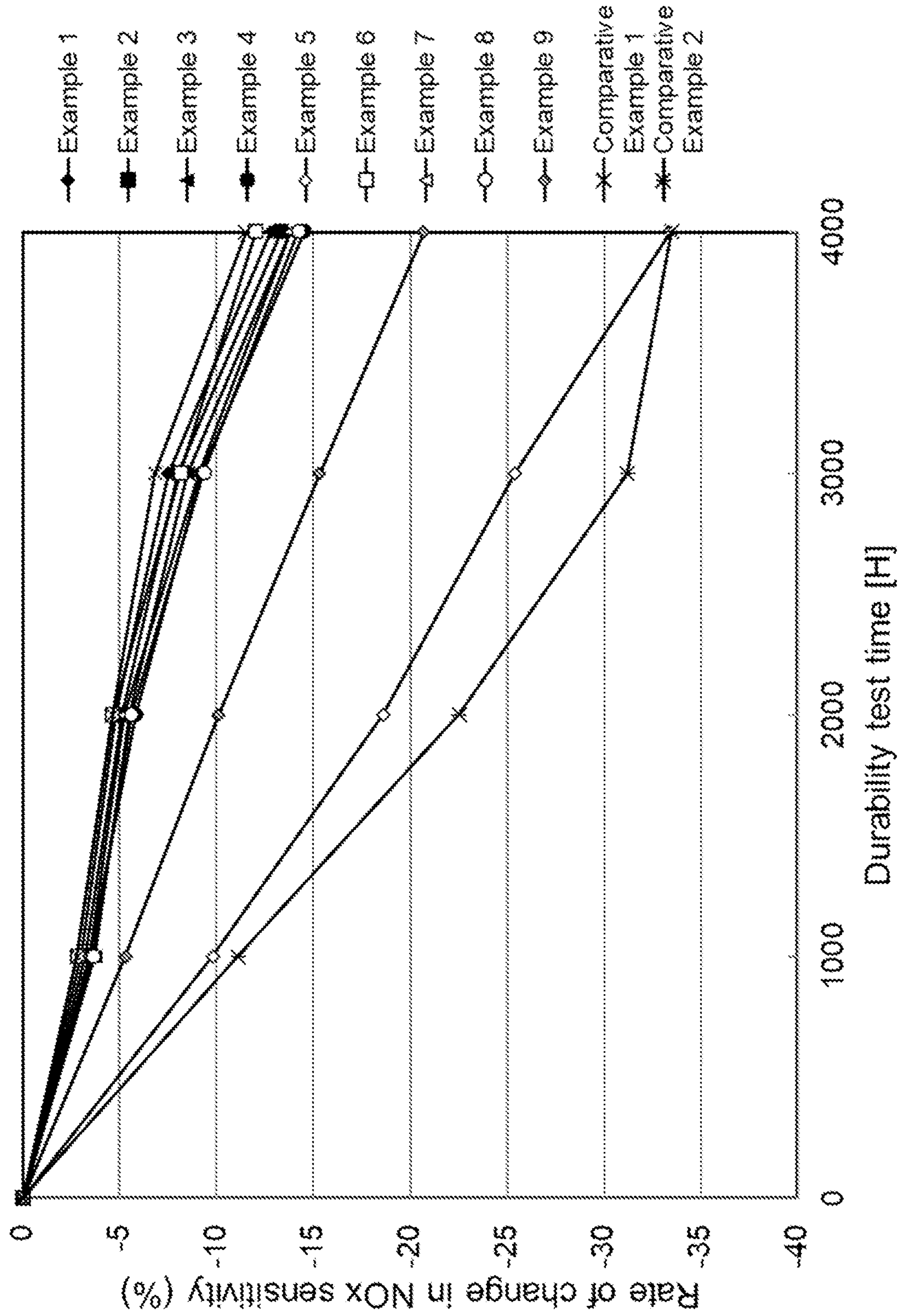
FIG. 8 is a graph showing durability test results of Examples 1 to 9 and Comparative Examples 1 to 2. The vertical axis of the graph represents the rate of change in NOx sensitivity (%) and the horizontal axis represents the durability time (hours; H).
Figure 9:
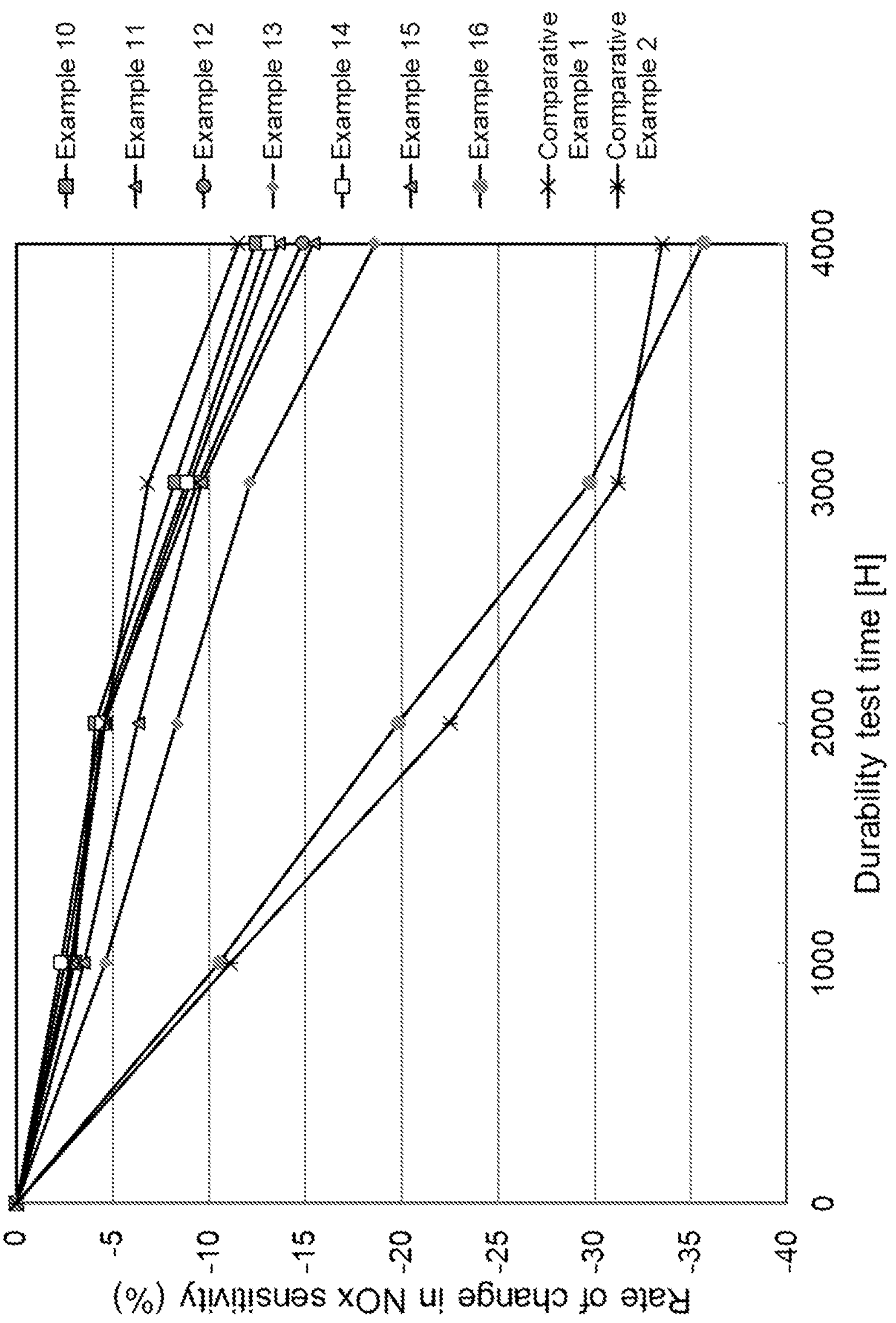
FIG. 9 is a graph showing durability test results of Examples 10 to 16 and Comparative Examples 1 to 2. The vertical axis of the graph represents the rate of change in NOx sensitivity (%) and the horizontal axis represents the durability test time (hours; H).

Table 1 shows the judgement results (Judgement 1 and Judgement 2) of Examples 1 to 16 and Comparative Examples 1 to 2, and rates of change in NOx sensitivity (%) after a lapse of 1000 hours, a lapse of 2000 hours, a lapse of 3000 hours and a lapse of 4000 hours of the durability test in Judgement test 2. As described above, Table 1 also shows an Au concentration relative to the total amount of Pt and Au in each of the high concentration region (A) and the low concentration region (B), a ratio ($L_A/L_1$) of the high concentration region (A) in the inner main pump electrode 22, and an Au concentration ratio ($C_A/C_B$), in each level. FIG. 8 shows the durability test results of Examples 1 to 9 and Comparative Examples 1 to 2. The vertical axis of the graph represents the rate of change in NOx sensitivity (%) and the horizontal axis represents the durability time (hours). FIG. 9 shows the durability test results of Examples 10 to 16 and Comparative Examples 1 to 2. The vertical axis of the graph represents the rate of change in NOx sensitivity (%) and the horizontal axis represents the durability test time (hours).

Examples 1 to 16 showed excellent results both in Judgement 1 and Judgement 2.

Thus, it was confirmed that excellent results are obtained both in the linearity $R^2$ of NOx detection current Ip2 in Judgement 1 and in the rate of change in NOx sensitivity in Judgement 2 when the ratio ($L_A/L_1$) of the total length ($L_A$) of the high concentration region (A) in the longitudinal direction of the sensor element 101 in the total length ($L=L_1$) of the inner oxygen pump electrode 90 (the inner main pump electrode 22) in the longitudinal direction of the sensor element 101 falls within the range of 15.0% to 90.0%.

That is, it was revealed that NOx can be detected with high accuracy even under high oxygen concentration. It was also revealed that the NOx detection sensitivity can be maintained even after a long term use.

Comparative Example 1 can be compared with Examples 1 to 5. In Comparative Example 1, the linearity $R^2$ of NOx detection current Ip2 in Judgement 1 was judged as D. On the other hand, the rate of change in NOx sensitivity in Judgement 2 was judged as A. In Comparative Example 1, the ratio ($L_A/L_1$) of the high concentration region (A) in the inner main pump electrode 22 was 5%. It is considered that in Comparative Example 1, NOx decomposed in the inner main pump electrode 22 since the high concentration region (A) was small relative to the region where the applied voltage Vp0 was locally large in the inner main pump electrode 22.

In Comparative Example 2, the high concentration region (A) and the low concentration region (B) had the same Au concentration of 0.75% by weight. In other words, the Au concentration in the metal material was 0.75% by weight in the whole area of the inner main pump electrode ($L_A/L_1$:

100%). In Comparative Example 2, the linearity $R^2$ of NOx detection current Ip2 in Judgement 1 was judged as A. On the other hand, the rate of change in NOx sensitivity in Judgement 2 was judged as D.

In Comparative Example 2, Au concentration is higher than in Examples 1 to 16 even at a position far from the front end of the sensor element 201 in the inner main pump electrode 22, namely at a position close to the measurement electrode 44. Therefore, it is inferred that the amount of Au evaporating from the inner main pump electrode 22 was large, and the amount of Au adhered to the measurement electrode 44 in the evaporated Au was also large during the durability test in Judgement test 2. As a result, it is considered that NOx decomposition performance in the measurement electrode 44 deteriorated after execution of the durability test. It is considered that not all of NOx in the measurement-object gas having reached the measurement electrode 44 could be decomposed, and the NOx detection current value Ip2 was smaller than the actual value after execution of the durability test. Therefore, it is considered that the rate of change in NOx sensitivity in Judgment 2 was large in Comparative Example 2.

Examples 17 to 21

As Examples 17 to 21, the sensor element 101 shown in FIG. 1 and FIG. 2 was manufactured according to the aforementioned production method of the sensor element 101. Table 2 shows a concentration (% by weight) of Au relative to the total amount of Pt and Au in the high concentration region (A); a concentration (% by weight) of Au relative to the total amount of Pt and Au in the low concentration region (B); a ratio $[(L_A/(L_1+L_2)](\%)$ of the length ($L_A$) of the high concentration region (A) in the longitudinal direction of the sensor element 101 to the total length ($L=L_1+L_2$) of the inner oxygen pump electrode 90 (inner main pump electrode 22 and auxiliary pump electrode 51) in the longitudinal direction of the sensor element 101; and a ratio (Au concentration ratio: $C_A/C_B$) of Au concentration ($C_A$) in the high concentration region (A) to Au concentration ($C_B$) in the low concentration region (B) in every level.

Specifically, as an electrode paste for the inner main pump electrode 22 and the auxiliary pump electrode 51, electrode pastes having different Au concentrations relative to the total amount of Pt and Au were prepared. The Au concentration relative to the total amount of Pt and Au in each electrode paste was 0.40% by weight, 0.50% by weight, 0.60% by weight, 0.80% by weight, 1.00% by weight, or 2.00% by weight.

In Examples 17 to 21, the ceiling electrode portion 22*a* and the bottom electrode portion 22*b* of the inner main pump electrode 22 had the same shape. In every level of Examples 17 to 21, the ceiling electrode portion 22*a* and the bottom electrode portion 22*b* each had a rectangle shape having the length ($L_1$) of 3.5 mm in the longitudinal direction of the sensor element 101, and the width of 2.5 mm perpendicular to the longitudinal direction of the sensor element 101. In every level, the thickness of the inner main pump electrode 22 was 15 μm.

In Examples 17 to 21, the ceiling electrode portion 51*a* and the bottom electrode portion 51*b* of the auxiliary pump electrode 51 had the same shape. In every standard of Examples 17 to 21, the ceiling electrode portion 51*a* and the bottom electrode portion 51*b* each had a rectangle shape having the length ($L_2$) of 2.0 mm in the longitudinal direction of the sensor element 101, and the width of 1.5 mm perpendicular to the longitudinal direction of the sensor element 101. In every level, the auxiliary pump electrode 51 had a thickness of 15 μm.

In each of Examples 17 to 21, an electrode paste having an Au concentration in each level was printed on the high concentration region (A) of ratio $[L_A/(L_1+L_2)]$ in each level in the inner main pump electrode 22 and the auxiliary pump electrode 51 as shown in Table 2. An electrode paste having an Au concentration in level standard was printed on the low concentration region (B) which is the remaining region in the inner main pump electrode 22 and the auxiliary pump electrode 51.

Except for the above, the sensor elements of Examples 17 to 21 were manufactured in the same manner as in Examples 1 to 16 and Comparative Examples 1 to 2 according to the aforementioned production method of the sensor element 101. Gas sensors of Examples 17 to 21 in which the manufactured sensor elements were incorporated were manufactured in the same manner as in Examples 1 to 16 and Comparative Examples 1 to 2.

Figure 10:
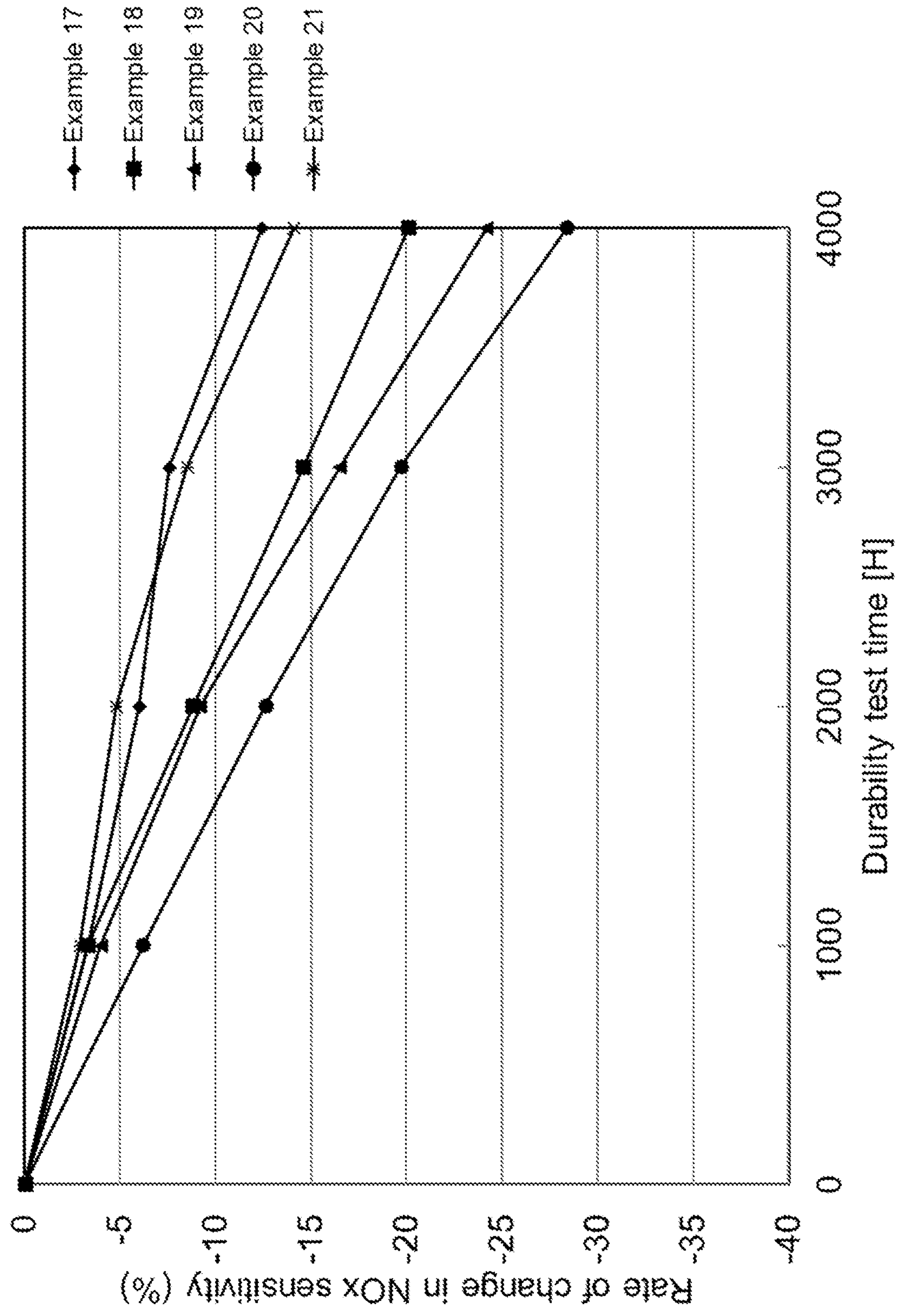
FIG. 10 is a graph showing durability test results of Examples 17 to 21. The vertical axis of the graph represents the rate of change in NOx sensitivity (%) and the horizontal axis represents the durability test time (hours; H).

The gas sensors of Examples 17 to 21 were subjected to Judgement test 1 and Judgement test 2 described above in the same manner as in Examples 1 to 16 and Comparative Examples 1 to 2. Table 2 shows the judgement results (Judgement 1 and Judgement 2) of Examples 17 to 21, and rates of change in NOx sensitivity (%) after a lapse of 1000 hours, a lapse of 2000 hours, a lapse of 3000 hours and a lapse of 4000 hours of the durability test in Judgement test 2. FIG. 10 shows the durability test results of Examples 17 to 21. The vertical axis of the graph represents the rate of change in NOx sensitivity (%) and the horizontal axis represents the durability test time (hours).

TABLE 2

| Level | Au concentration [wt. %] in high concentration region (A) | Au concentration [wt. %] in low concentration region (B) | a ratio $[L_A/(L_1 + L_2)]$ (%) of high concentration region (A) to total of inner oxygen pump electrode | Au concentration ratio ($C_A/C_B$) | Judgement 1 | Judgement 2 | Rate of change in NOx sensitivity (%) in Judgement test 2: 1000 hrs | 2000 hrs | 3000 hrs | 4000 hrs |
|---|---|---|---|---|---|---|---|---|---|---|
| Example 17 | 0.80 | 0.50 | 65.0 | 1.6 | A | A | −3.3 | −6.0 | −7.6 | −12.4 |
| Example 18 | 0.80 | 0.50 | 80.0 | 1.6 | A | B | −3.3 | −8.8 | −14.6 | −20.1 |
| Example 19 | 1.00 | 0.50 | 80.0 | 2.0 | A | B | −4.0 | −9.2 | −16.5 | −24.2 |
| Example 20 | 2.00 | 0.40 | 80.0 | 5.0 | A | B | −6.2 | −12.6 | −19.7 | −28.4 |
| Example 21 | 0.60 | 0.40 | 40.0 | 1.5 | B | A | −2.9 | −4.8 | −8.5 | −14.1 |

Examples 17 to 21 showed excellent results both in Judgement 1 and Judgement 2.

The sensor element 201 of Examples 1 to 16 adjusts the oxygen partial pressure in the measurement-object gas to a value that does not substantially affect measurement of NOx in the measurement electrode 44 by operating the main pump cell 21. The inner oxygen pump electrode 90 in the sensor element 201 is the inner main pump electrode 22. Meanwhile, the sensor element 101 of Examples 17 to 21 adjusts the oxygen partial pressure in the measurement-object gas to a value that does not substantially affect measurement of NOx in the measurement electrode 44 by operating the main pump cell 21 and the auxiliary pump cell 50. The inner oxygen pump electrode 90 in the sensor element 101 is the inner main pump electrode 22 and the auxiliary pump electrode 51.

Examples 1 to 16 and Examples 17 to 21 showed excellent results both in Judgement 1 and Judgement 2. In other words, it was confirmed that excellent results are obtained both in the linearity $R^2$ of NOx detection current Ip2 in Judgement 1 and in the rate of change in NOx sensitivity in Judgement 2 by making the high concentration region (A) satisfy a predetermined range in a whole of the inner oxygen pump electrode 90.

Examples 22 to 26

As Examples 22 to 26, the sensor element 301 shown in FIG. 5 and FIG. 6 was manufactured according to the aforementioned production method of the sensor element 101. In the sensor element 301, the inner main pump electrode 22 is disposed facing with the one internal cavity 14 at a position close to the front end part of the sensor element 301 on the lower surface of the second solid electrolyte layer 6. Also, the auxiliary pump electrode 51 and the measurement electrode 44 are disposed in parallel in the longitudinal direction of the sensor element 301 at a position farther from the front end part of the sensor element 301 than the inner main pump electrode 22 on the upper surface of the first solid electrolyte layer 4.

Table 3 shows a concentration (% by weight) of Au relative to the total amount of Pt and Au in the high concentration region (A); a concentration (% by weight) of Au relative to the total amount of Pt and Au in the low concentration region (B); a ratio $[(L_A/(L_1+L_2)](\%)$ of the total length ($L_A$) of the high concentration region (A) in the longitudinal direction of the sensor element 101 in the total length ($L=L_1+L_2$) of the inner oxygen pump electrode (inner main pump electrode 22 and auxiliary pump electrode 51) in the longitudinal direction of the sensor element 101; and a ratio (Au concentration ratio: $C_A/C_B$) of Au concentration ($C_A$) in the high concentration region (A) to Au concentration ($C_B$) in the low concentration region (B) in every level.

Specifically, as an electrode paste for the inner main pump electrode 22 and the auxiliary pump electrode 51, electrode pastes having different Au concentrations relative to the total amount of Pt and Au were prepared. The Au concentration relative to the total amount of Pt and Au in each electrode paste was 0.20% by weight, 0.30% by weight, 0.50% by weight, 0.60% by weight, 1.00% by weight, or 2.00% by weight.

In every level of Examples 22 to 26, the inner main pump electrode 22 each had a rectangle shape having the length ($L_1$) of 5.0 mm in the longitudinal direction of the sensor element 301, and the width of 2.0 mm perpendicular to the longitudinal direction of the sensor element 301. In every level, the thickness of the inner main pump electrode 22 was 15 μm.

In every level of Examples 22 to 26, the auxiliary pump electrode 51 each had a rectangle shape having the length ($L_2$) of 1.5 mm in the longitudinal direction of the sensor element 301, and the width of 0.5 mm perpendicular to the longitudinal direction of the sensor element 301. In every level, the auxiliary pump electrode 51 had a thickness of 15 μm.

In each of Examples 22 to 26, an electrode paste having an Au concentration in each level was printed on the high concentration region (A) of ratio $[L_A/(L_1+L_2)]$ in each level in the inner main pump electrode 22 and the auxiliary pump electrode 51 as shown in Table 3. An electrode paste having an Au concentration in each level was printed on the low concentration region (B) which is the remaining region in the inner main pump electrode 22 and the auxiliary pump electrode 51.

Except for the above, the sensor elements of Examples 22 to 26 were manufactured in the same manner as in Examples 1 to 16 and Comparative Examples 1 to 2 according to the aforementioned production method of the sensor element 101. Gas sensors of Examples 22 to 26 in which the manufactured sensor elements were incorporated were manufactured in the same manner as in Examples 1 to 16 and Comparative Examples 1 to 2.

Figure 11:
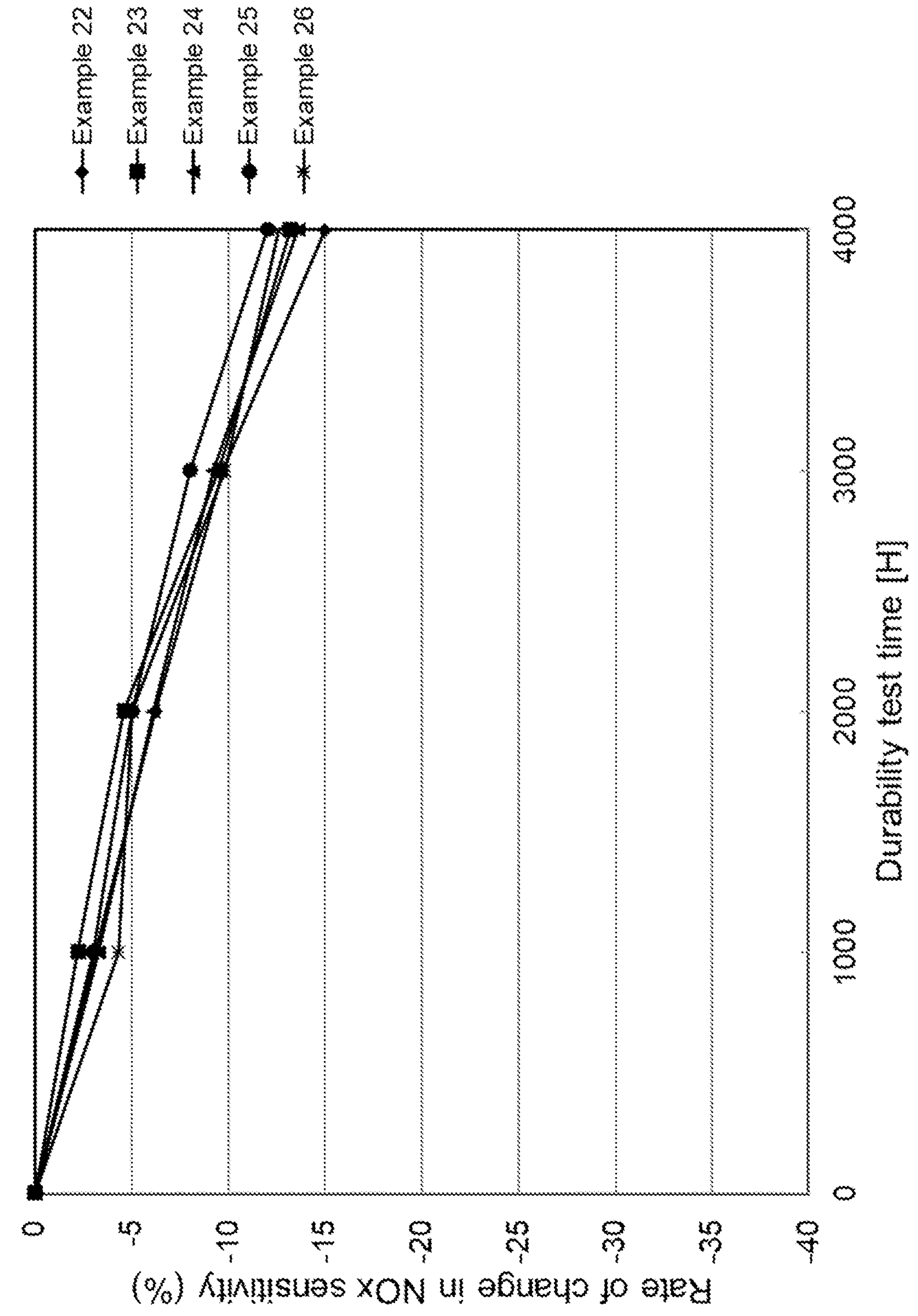
FIG. 11 is a graph showing durability test results of Examples 22 to 26. The vertical axis of the graph represents the rate of change in NOx sensitivity (%) and the horizontal axis represents the durability test time (hours).

The gas sensors of Examples 22 to 26 were subjected to Judgement test 1 and Judgement test 2 described above in the same manner as in Examples 1 to 16 and Comparative Examples 1 to 2. Table 3 shows the judgement results (Judgement 1 and Judgement 2) of Examples 22 to 26, and rates of change in NOx sensitivity (%) after a lapse of 1000 hours, a lapse of 2000 hours, a lapse of 3000 hours and a lapse of 4000 hours of the durability test in Judgement test 2. FIG. 11 shows the durability test results of Examples 22 to 26. The vertical axis of the graph represents the rate of change in NOx sensitivity (%) and the horizontal axis represents the durability test time (hours).

TABLE 3

| Level | Au concentration [wt. %] in high concentration region (A) | Au concentration [wt. %] in low concentration region (B) | a ratio $[L_A/(L_1+L_2)]$ (%) of high concentration region (A) to total of inner oxygen pump electrode | Au concentration ratio ($C_A/C_B$) | Judgement 1 | Judgement 2 | Rate of change in NOx sensitivity (%) in Judgement test 2: 1000 hrs | 2000 hrs | 3000 hrs | 4000 hrs |
|---|---|---|---|---|---|---|---|---|---|---|
| Example 22 | 0.60 | 0.30 | 80.0 | 2.0 | A | A | −3.1 | −6.2 | −9.7 | −15.0 |
| Example 23 | 0.50 | 0.20 | 80.0 | 2.5 | A | A | −2.2 | −4.6 | −9.5 | −13.2 |

TABLE 3-continued

| Level | Au concentration [wt. %] in high concentration region (A) | Au concentration [wt. %] in low concentration region (B) | a ratio $[L_A/(L_1 + L_2)]$ (%) of high concentration region (A) to total of inner oxygen pump electrode | Au concentration ratio $(C_A/C_B)$ | Judgement 1 | Judgement 2 | Rate of change in NOx sensitivity (%) in Judgement test 2: 1000 hrs | 2000 hrs | 3000 hrs | 4000 hrs |
|---|---|---|---|---|---|---|---|---|---|---|
| Example 24 | 1.00 | 0.50 | 60.0 | 2.0 | A | A | −3.3 | −6.1 | −9.2 | −13.6 |
| Example 25 | 0.60 | 0.30 | 30.0 | 2.0 | B | A | −3.0 | −5.0 | −8.0 | −12.0 |
| Example 26 | 2.00 | 0.50 | 50.0 | 4.0 | A | A | −4.3 | −5.0 | −9.8 | −12.6 |

Examples 22 to 26 showed excellent results both in Judgement 1 and Judgement 2.

In the sensor element 301 of Examples 22 to 26, the auxiliary pump electrode 51 and the measurement electrode 44 are disposed in parallel in the longitudinal direction of the sensor element 301 at positions farther from the front end part of the sensor element 301 than the inner main pump electrode 22. Meanwhile, in the sensor element 101 of Examples 17 to 21, the auxiliary pump electrode 51 and the measurement electrode 44 are disposed in series in this order at positions farther from the front end part of the sensor element 101 than the inner main pump electrode 22.

Examples 17 to 21 and Examples 22 to 26 showed excellent results both in Judgement 1 and Judgement 2. In other words, it was confirmed that excellent results are obtained both in the linearity $R^2$ of NOx detection current Ip2 in Judgement 1 and in the rate of change in NOx sensitivity in Judgement 2 by making the high concentration region (A) satisfy a predetermined range as a whole of the inner oxygen pump electrode 90, even when the auxiliary pump electrode 51 is disposed in parallel with the measurement electrode 44 as in Examples 22 to 26.

What is claimed is:

1. A sensor element for detecting NOx in a measurement-object gas, the sensor element comprising:

a base part in an elongated plate shape, including a plurality of oxygen-ion-conductive solid electrolyte layers stacked;

a measurement-object gas flow part for introduction and flow of the measurement-object gas through a gas inlet formed in one end part in a longitudinal direction of the base part;

an inner oxygen pump electrode disposed on an inner surface of the measurement-object gas flow part; and a measurement electrode disposed on the inner surface of the measurement-object gas flow part, wherein the inner oxygen pump electrode has a predetermined length (L) in the longitudinal direction and includes:

a region (A) including an electrode end close to the gas inlet and having a predetermined length $(L_A)$ in the longitudinal direction, and a region (B) including an electrode end far from the gas inlet and having a predetermined length $(L_B)$ in the longitudinal direction;

the inner oxygen pump electrode comprises a metal material, the metal material including an activity reducing metal that reduces catalytic activity of decomposing NOx;

a content of the activity reducing metal in the metal material in the region (A) is higher than a content of the activity reducing metal in the metal material in the region (B); and a ratio $(L_A/L)$ of the length $(L_A)$ in the longitudinal direction of the region (A) of the inner oxygen pump electrode to the length (L) in the longitudinal direction of the inner oxygen pump electrode is 15% to less than or equal to 60%, and wherein the content of the activity reducing metal in the metal material in the region (A) is 1.0% by weight to 2.0% by weight.

2. The sensor element according to claim 1, wherein the inner oxygen pump electrode comprises a plurality of electrodes disposed on the inner surface of the measurement-object gas flow part, and the length (L) in the longitudinal direction of the inner oxygen pump electrode is a sum of respective lengths in the longitudinal direction of the plurality of electrodes.

3. The sensor element according to claim 1, wherein the inner oxygen pump electrode comprises:

an inner main pump electrode disposed on the inner surface of the measurement-object gas flow section, and an auxiliary pump electrode disposed at a position farther from the gas inlet than the inner main pump electrode on the inner surface of the measurement-object gas flow part, and the length (L) in the longitudinal direction of the inner oxygen pump electrode is a sum $(L_1+L_2)$ of a length $(L_1)$ in the longitudinal direction of the inner main pump electrode and a length $(L_2)$ in the longitudinal direction of the auxiliary pump electrode.

4. The sensor element according to claim 3, wherein the auxiliary pump electrode and the measurement electrode are disposed in this order in series in the longitudinal direction at positions farther from the gas inlet than the inner main pump electrode on the inner surface of the measurement-object gas flow part.

5. The sensor element according to claim 3, wherein the auxiliary pump electrode and the measurement electrode are disposed in parallel in the longitudinal direction at positions farther from the gas inlet than the inner main pump electrode on the inner surface of the measurement-object gas flow part.

6. The sensor element according to claim 1, wherein the ratio $(L_A/L)$ of the length $(L_A)$ in the longitudinal direction of the region (A) of the inner oxygen pump electrode to the length (L) in the longitudinal direction of the inner oxygen pump electrode is 30% to less than or equal to 60%.

7. The sensor element according to claim 1, wherein the activity reducing metal comprises at least one selected from the group consisting of gold and silver.

8. The sensor element according to claim 1, wherein the content of the activity reducing metal in the metal material in the region (B) of the inner oxygen pump electrode is 0.1% by weight to 0.5% by weight, provided that the content of the activity reducing metal in the metal material in the region (B) is lower than the content of the activity reducing metal in the metal material in the region (A).

9. The sensor element according to claim 1, wherein a ratio ($C_A/C_B$) of the content ($C_A$) of the activity reducing metal in the metal material in the region (A) to the content ($C_B$) of the activity reducing metal in the metal material in the region (B) of the inner oxygen pump electrode is not less than 1.5 and not more than 20.0.

* * * * *